(12) United States Patent
Hawson et al.

(10) Patent No.: US 11,554,215 B2
(45) Date of Patent: Jan. 17, 2023

(54) INJECTION DEVICE AND INJECTION SOLUTION TRANSFERRING SYSTEM

(71) Applicant: NOVARTIS AG, Basel (CH)

(72) Inventors: Nicholas Lee Hawson, Cambridge (GB); Martin Murphy, Cambridge (GB); Frederick William Hamlin, Cambridge (GB); Christophe Royer, Basel (CH); Dominic Lloyd-Lucas, Cambridge (GB); Tony Bedford, Cambridge (GB); Andrew Gow, Cambridge (GB); Dave Harris, Cambridge (GB); Duncan Aleck Bishop, Cambridge (GB); Matthew Garwood, Cambridge (GB); Matthew Murchie, Cambridge (GB); Lasse Mogensen, Cambridge (GB)

(73) Assignee: Novartis AG, Basel (CH)

( * ) Notice: Subject to any disclaimer, the term of this patent is extended or adjusted under 35 U.S.C. 154(b) by 553 days.

(21) Appl. No.: 16/620,334

(22) PCT Filed: Jun. 8, 2018

(86) PCT No.: PCT/EP2018/065144
§ 371 (c)(1),
(2) Date: Dec. 6, 2019

(87) PCT Pub. No.: WO2018/224644
PCT Pub. Date: Dec. 13, 2018

(65) Prior Publication Data
US 2020/0188589 A1    Jun. 18, 2020

(30) Foreign Application Priority Data

Jun. 8, 2017 (EP) .................................. 17174979
Jun. 8, 2017 (EP) .................................. 17174984

(51) Int. Cl.
*A61M 5/178* (2006.01)
*A61M 5/24* (2006.01)
(Continued)

(52) U.S. Cl.
CPC ............ *A61M 5/1782* (2013.01); *A61M 5/24* (2013.01); *A61J 1/20* (2013.01); *A61M 5/20* (2013.01);
(Continued)

(58) Field of Classification Search
CPC .......... A61J 1/20; A61M 5/20; A61M 5/1782; A61M 5/24; A61M 5/31511;
(Continued)

(56) References Cited

U.S. PATENT DOCUMENTS 3,608,550 A * 9/1971 Stawski ................ A61J 1/2096
604/414
3,729,031 A    4/1973 Baldwin
(Continued)

FOREIGN PATENT DOCUMENTS

AT    178217 T    4/1999
AT    193215 T    6/2000
(Continued)

OTHER PUBLICATIONS

Novartis AG, International Patent Application No. PCT/EP2018/065144, International Search Report, dated Oct. 12, 2018.
(Continued)

*Primary Examiner* — Tasnim Mehjabin Ahmed
(74) *Attorney, Agent, or Firm* — Dentons US LLP

(57) ABSTRACT

An injection device (10) comprises an injection solution receptacle (30) and a plunger (70) at least a portion of which is slidably received in the injection solution receptacle (30), wherein the plunger (70) is displaceable relative to the injection solution receptacle (30) in a distal direction in
(Continued)

order to expel an injection solution contained in the injection solution receptacle (30) from the injection solution receptacle (30). A first plunger stop mechanism (140) is adapted to stop a displacement of the plunger (70) relative to the injection solution receptacle (30) in the distal direction at a first dosing position (P1). A second plunger stop mechanism (140) is adapted to stop a displacement of the plunger (70) relative to the injection solution receptacle (30) from the first dosing position (P1) in the distal direction at a second dosing position (P2), wherein the first and the second dosing position (P2) of the plunger (70) are selected in such a manner that the plunger (70), upon being displaced relative to the injection solution receptacle (30) between the first and the second dosing position (P2) is adapted to expel a desired dose of the injection solution contained in the injection solution receptacle (30) from the injection solution receptacle (30).

13 Claims, 18 Drawing Sheets

(51) Int. Cl.
  *A61J 1/20* (2006.01)
  *A61M 5/20* (2006.01)
  *A61M 5/315* (2006.01)
  *A61M 5/31* (2006.01)
(52) U.S. Cl.
  CPC ..... *A61M 5/31511* (2013.01); *A61M 5/31551* (2013.01); *A61M 2005/2488* (2013.01); *A61M 2005/3104* (2013.01); *A61M 2005/3126* (2013.01); *A61M 2205/581* (2013.01); *A61M 2207/00* (2013.01); *A61M 2209/045* (2013.01)
(58) Field of Classification Search
  CPC ...... A61M 5/31551; A61M 2005/2488; A61M 2005/3104; A61M 2205/581
  See application file for complete search history.

(56) References Cited

U.S. PATENT DOCUMENTS

| | | | |
|---|---|---|---|
| 4,475,905 A * | 10/1984 | Himmelstrup | A61M 5/31551 604/263 |
| 5,807,374 A | 9/1998 | Caizza et al. | |
| 5,820,602 A | 10/1998 | Kovelman et al. | |
| 5,928,215 A | 7/1999 | Caizza et al. | |
| 6,090,071 A | 7/2000 | Kriesel | |
| 6,149,623 A | 11/2000 | Reynolds | |
| 6,174,304 B1 | 1/2001 | Weston | |
| 6,638,244 B1 | 10/2003 | Reynolds | |
| 6,663,602 B2 | 12/2003 | Moller | |
| 6,681,810 B2 | 1/2004 | Weston | |
| 6,685,693 B1 | 2/2004 | Casso | |
| 7,241,278 B2 | 7/2007 | Moller | |
| 7,470,258 B2 | 12/2008 | Barker et al. | |
| 7,736,343 B2 | 6/2010 | Marshall et al. | |
| 7,811,263 B2 | 10/2010 | Burren et al. | |
| 7,867,202 B2 | 1/2011 | Moser et al. | |
| 7,896,850 B2 | 3/2011 | Kronestedt et al. | |
| 8,202,256 B2 | 6/2012 | Moller | |
| 8,206,361 B2 | 6/2012 | Moller | |
| 8,267,899 B2 | 9/2012 | Moller | |
| 8,333,739 B2 | 12/2012 | Moller | |
| 8,409,138 B2 | 4/2013 | James et al. | |
| 8,617,109 B2 | 12/2013 | Kronestedt et al. | |
| 8,869,635 B2 | 10/2014 | Daniel et al. | |
| 8,973,621 B2 | 3/2015 | Matusch | |
| 9,011,386 B2 | 4/2015 | Kronestedt et al. | |
| 9,022,991 B1 | 5/2015 | Moeller | |
| 2001/0051793 A1 | 12/2001 | Weston | |
| 2002/0052578 A1 | 5/2002 | Moller | |
| 2002/0177819 A1 | 11/2002 | Barker et al. | |
| 2004/0024354 A1 | 2/2004 | Reynolds | |
| 2004/0059299 A1 | 3/2004 | Moller | |
| 2005/0090782 A1 | 4/2005 | Marshall et al. | |
| 2005/0209570 A1 | 9/2005 | Moller | |
| 2006/0276753 A1 | 12/2006 | Kronestedt et al. | |
| 2006/0276754 A1 | 12/2006 | Kronestedt et al. | |
| 2007/0016142 A1 | 1/2007 | Burren et al. | |
| 2007/0021718 A1 | 1/2007 | Burren et al. | |
| 2007/0244445 A1 | 10/2007 | Moller | |
| 2008/0065026 A1 | 3/2008 | Moller | |
| 2008/0071227 A1 | 3/2008 | Moser et al. | |
| 2008/0077094 A1 | 3/2008 | Burren et al. | |
| 2008/0183138 A1 | 7/2008 | Moser et al. | |
| 2008/0281275 A1 | 11/2008 | Moller | |
| 2009/0308386 A1 | 12/2009 | Kronestedt et al. | |
| 2010/0049125 A1 | 2/2010 | James et al. | |
| 2010/0186739 A1 | 7/2010 | Kronestedt et al. | |
| 2011/0214777 A1 | 9/2011 | Matusch | |
| 2012/0152039 A1 | 6/2012 | Daniel et al. | |
| 2012/0226240 A1 | 9/2012 | Bedford et al. | |
| 2013/0079728 A1 | 3/2013 | Moeller | |
| 2013/0289518 A1 | 10/2013 | Butler et al. | |
| 2014/0150925 A1 | 6/2014 | Sjögren et al. | |
| 2014/0330204 A1 | 11/2014 | Huculak et al. | |
| 2015/0100028 A1 | 4/2015 | Moeller | |
| 2015/0157801 A1 | 6/2015 | Tran et al. | |
| 2015/0297453 A1 | 10/2015 | Kim et al. | |
| 2015/0297455 A1 | 10/2015 | Sanders et al. | |
| 2015/0297881 A1 | 10/2015 | Sanders et al. | |
| 2015/0311624 A1 | 10/2015 | Keil | |
| 2016/0001004 A1 | 1/2016 | Fourt et al. | |
| 2016/0151578 A1 | 6/2016 | Oakley et al. | |

FOREIGN PATENT DOCUMENTS

| | | |
|---|---|---|
| AT | 217181 T | 5/2002 |
| AT | 303831 T | 9/2005 |
| AT | 401921 T | 8/2008 |
| AU | 725917 B2 | 10/2000 |
| AU | 726244 B2 | 11/2000 |
| AU | 2001273890 B2 | 7/2005 |
| AU | 2006218064 A1 | 8/2006 |
| AU | 2006251769 A1 | 11/2006 |
| AU | 2008226638 A1 | 9/2008 |
| AU | 2006218064 B2 | 5/2009 |
| AU | 2006251769 B2 | 7/2009 |
| AU | 2009217376 A1 | 10/2009 |
| AU | 2009217376 B2 | 1/2013 |
| AU | 2008226638 B2 | 3/2013 |
| AU | 2011315626 A1 | 4/2013 |
| AU | 2011315626 B2 | 1/2015 |
| AU | 2014241449 A1 | 8/2015 |
| AU | 2014328035 A1 | 4/2016 |
| BE | 726863 A | 7/1969 |
| BR | PI9510212-4 A | 11/1997 |
| BR | PI9802604-6 A | 11/1999 |
| BR | PI0208064-8 A | 10/2006 |
| BR | PI0808709-1 A2 | 9/2014 |
| CA | 2231481 A1 | 3/1997 |
| CA | 2207991 C | 8/2001 |
| CA | 2242915 C | 8/2001 |
| CA | 2412229 A1 | 12/2001 |
| CA | 2243021 C | 3/2002 |
| CA | 2440888 A1 | 9/2002 |
| CA | 2231481 C | 1/2008 |
| CA | 2680335 A1 | 9/2008 |
| CA | 2412229 C | 8/2010 |
| CA | 2678198 A1 | 3/2011 |
| CA | 2813277 A1 | 4/2012 |
| CA | 2680335 C | 1/2014 |
| CA | 2899558 A1 | 10/2014 |
| CA | 2929376 A1 | 5/2015 |
| CH | 492215 A | 6/1970 |
| CN | 1175217 A | 3/1998 |
| CN | 1197398 A | 10/1998 |
| CN | 1441684 A | 9/2003 |
| CN | 1509192 A | 6/2004 |

(56) References Cited

FOREIGN PATENT DOCUMENTS

| | | |
|---|---|---|
| CN | 1188181 C | 2/2005 |
| CN | 101124005 A | 2/2008 |
| CN | 101184521 A | 5/2008 |
| CN | 101641125 A | 2/2010 |
| CN | 101124005 B | 12/2010 |
| CN | 202113444 U | 1/2012 |
| CN | 101184521 B | 2/2012 |
| CN | 102946930 A | 2/2013 |
| CN | 101641125 B | 6/2013 |
| CN | 103260675 A | 8/2013 |
| CN | 105025958 A | 11/2015 |
| CN | 103260675 B | 1/2016 |
| CN | 105377329 A | 3/2016 |
| DE | 1901633 A1 | 9/1969 |
| DE | 2021253 A1 | 11/1970 |
| DE | 8509572 U1 | 8/1985 |
| DE | 69508792 T2 | 8/1999 |
| DE | 69608567 T2 | 2/2001 |
| DE | 69712499 T2 | 11/2002 |
| DE | 69808205 T2 | 5/2003 |
| DE | 60113256 T2 | 6/2006 |
| DE | 102005008065 A1 | 8/2006 |
| DE | 102005023823 A1 | 11/2006 |
| DE | 102005023854 A1 | 11/2006 |
| DE | 102005032705 A1 | 11/2006 |
| DE | 102005044096 A1 | 11/2006 |
| DE | 102005032705 B4 | 1/2009 |
| DE | 102005063497 B4 | 9/2009 |
| DE | 202005021773 U1 | 1/2010 |
| DE | 102010010699 A1 | 9/2011 |
| DK | 124660 B | 11/1972 |
| DK | 0799063 T3 | 10/1999 |
| DK | 0850079 T3 | 11/2000 |
| DK | 928182 T3 | 8/2002 |
| DK | 1294418 T3 | 1/2006 |
| DK | 1728529 T3 | 11/2008 |
| DK | 1855742 T3 | 4/2009 |
| DK | 1888149 T3 | 6/2009 |
| DK | 1855740 T3 | 7/2009 |
| DK | 1885414 T3 | 2/2013 |
| EA | 201591482 A1 | 1/2016 |
| EP | 0799063 A1 | 10/1997 |
| EP | 0850079 A1 | 7/1998 |
| EP | 0896826 A1 | 2/1999 |
| EP | 0799063 B1 | 3/1999 |
| EP | 0928182 A1 | 7/1999 |
| EP | 0850079 B1 | 5/2000 |
| EP | 0928182 B1 | 5/2002 |
| EP | 0896826 B1 | 9/2002 |
| EP | 1294418 A1 | 3/2003 |
| EP | 1372756 A2 | 1/2004 |
| EP | 1463550 A2 | 10/2004 |
| EP | 1568389 A1 | 8/2005 |
| EP | 1294418 B1 | 9/2005 |
| EP | 1690561 A2 | 8/2006 |
| EP | 1690561 A3 | 12/2006 |
| EP | 1728529 A1 | 12/2006 |
| EP | 1885414 A1 | 2/2008 |
| EP | 1885415 A1 | 2/2008 |
| EP | 1372756 A4 | 5/2008 |
| EP | 1728529 B1 | 7/2008 |
| EP | 1855742 B1 | 12/2008 |
| EP | 1888149 B1 | 2/2009 |
| EP | 1855740 B1 | 3/2009 |
| EP | 2134391 A2 | 12/2009 |
| EP | 2364742 A2 | 9/2011 |
| EP | 1885415 A4 | 2/2012 |
| EP | 1885414 A4 | 4/2012 |
| EP | 2475454 A1 | 7/2012 |
| EP | 2484395 A2 | 8/2012 |
| EP | 1885414 B1 | 11/2012 |
| EP | 2364742 A3 | 11/2012 |
| EP | 2526987 A2 | 11/2012 |
| EP | 2484395 A3 | 4/2013 |
| EP | 2526987 A3 | 4/2013 |
| EP | 1885415 B1 | 5/2013 |
| EP | 2627377 A1 | 8/2013 |
| EP | 2475454 B1 | 11/2015 |
| EP | 2968766 A1 | 1/2016 |
| EP | 3021900 A1 | 5/2016 |
| EP | 3035983 A2 | 6/2016 |
| ES | 2129881 T3 | 6/1999 |
| ES | 2149499 T3 | 11/2000 |
| ES | 2176661 T3 | 12/2002 |
| ES | 2185115 T3 | 4/2003 |
| ES | 2249442 T3 | 4/2006 |
| ES | 2314568 T3 | 3/2009 |
| ES | 2423199 T3 | 9/2013 |
| FR | 2000286 A1 | 9/1969 |
| FR | 2046102 A5 | 3/1971 |
| GB | 1261751 A | 1/1972 |
| GB | 1267419 A | 3/1972 |
| JP | 10-510740 A | 10/1998 |
| JP | 11-114064 A | 4/1999 |
| JP | 11-510087 A | 9/1999 |
| JP | 11-512303 A | 10/1999 |
| JP | 2001-505072 A | 4/2001 |
| JP | 3450011 B2 | 9/2003 |
| JP | 2004-49726 A | 2/2004 |
| JP | 2004-503303 A | 2/2004 |
| JP | 2005-508656 A | 4/2005 |
| JP | 2005-514120 A | 5/2005 |
| JP | 3835817 B2 | 10/2006 |
| JP | 2006-326309 A | 12/2006 |
| JP | 2006-329423 A | 12/2006 |
| JP | 2008-529688 A | 8/2008 |
| JP | 2008-532581 A | 8/2008 |
| JP | 2008-541803 A | 11/2008 |
| JP | 2008-541931 A | 11/2008 |
| JP | 2008-541932 A | 11/2008 |
| JP | 4187790 B2 | 11/2008 |
| JP | 4357611 B2 | 11/2009 |
| JP | 2010-520786 A | 6/2010 |
| JP | 4550424 B2 | 7/2010 |
| JP | 4519803 B2 | 8/2010 |
| JP | 4575327 B2 | 11/2010 |
| JP | 4755247 B2 | 6/2011 |
| JP | 2011-156369 A | 8/2011 |
| JP | 2011-183163 A | 9/2011 |
| JP | 4837874 B2 | 10/2011 |
| JP | 5026411 B2 | 6/2012 |
| JP | 5026412 B2 | 6/2012 |
| JP | 5118222 B2 | 10/2012 |
| JP | 2013-511309 A | 4/2013 |
| JP | 5362591 B2 | 9/2013 |
| JP | 2013-539697 A | 10/2013 |
| JP | 5881958 B2 | 2/2016 |
| JP | 5897016 B2 | 3/2016 |
| JP | 2016-517301 A | 6/2016 |
| KR | 2003-0020299 A | 3/2003 |
| KR | 10-0721549 B1 | 5/2007 |
| KR | 10-2009-0109581 A | 10/2009 |
| KR | 10-1160735 B1 | 7/2012 |
| KR | 10-2015-0119092 A | 10/2015 |
| MX | 9704576 A | 7/1998 |
| MX | PA03007940 A | 10/2004 |
| MX | 2009009494 A | 9/2009 |
| NL | 6800629 A | 7/1969 |
| NO | 312175 B1 | 4/2002 |
| NO | 20025994 L | 2/2003 |
| NO | 334665 B1 | 5/2014 |
| NZ | 330879 A | 1/2000 |
| RU | 2155609 C2 | 9/2000 |
| RU | 2270698 C2 | 2/2006 |
| TW | 503117 B | 9/2002 |
| TW | 201215424 A | 4/2012 |
| WO | 1996/19252 A1 | 6/1996 |
| WO | 1997/01362 A2 | 1/1997 |
| WO | 1997/09080 A1 | 3/1997 |
| WO | 1997/25015 A1 | 7/1997 |
| WO | 1997/46202 A1 | 12/1997 |
| WO | 2001/95959 A1 | 12/2001 |
| WO | 2002/072173 A2 | 9/2002 |
| WO | 2003/057285 A2 | 7/2003 |

(56) References Cited

FOREIGN PATENT DOCUMENTS

| WO | 2002/072173 A3 | 10/2003 |
| --- | --- | --- |
| WO | 2003/057285 A3 | 12/2003 |
| WO | 2004/032996 A2 | 4/2004 |
| WO | 2004/032997 A2 | 4/2004 |
| WO | 2004/032997 A3 | 6/2004 |
| WO | 2004/032996 A3 | 7/2004 |
| WO | 2005/123162 A1 | 12/2005 |
| WO | 2006/089437 A1 | 8/2006 |
| WO | 2006/089734 A1 | 8/2006 |
| WO | 2006/125329 A1 | 11/2006 |
| WO | 2006/130098 A1 | 12/2006 |
| WO | 2006/130100 A1 | 12/2006 |
| WO | 2008/112472 A2 | 9/2008 |
| WO | 2008/112472 A3 | 11/2008 |
| WO | 2010/146358 A2 | 12/2010 |
| WO | 2011/029184 A1 | 3/2011 |
| WO | 2011/073174 A1 | 6/2011 |
| WO | 2011/073176 A1 | 6/2011 |
| WO | 2011073174 A1 | 6/2011 |
| WO | 2011073176 A1 | 6/2011 |
| WO | 2010/146358 A3 | 8/2011 |
| WO | 2012/049141 A1 | 4/2012 |
| WO | 2014/159017 A1 | 10/2014 |
| WO | 2014/162551 A1 | 10/2014 |
| WO | 2015/007808 A1 | 1/2015 |
| WO | 2015/047758 A2 | 4/2015 |
| WO | 2015047758 A2 | 4/2015 |
| WO | 2015/067548 A1 | 5/2015 |
| WO | 2015/047758 A3 | 7/2015 |
| WO | 2015/164377 A1 | 10/2015 |
| WO | 2015/164413 A1 | 10/2015 |
| WO | 2015/164416 A1 | 10/2015 |
| WO | 2018/224644 A1 | 12/2018 |
| ZA | 2002/9998 B | 12/2003 |

OTHER PUBLICATIONS

Novartis AG, International Patent Application No. PCT/EP2018/065144, Written Opinion, dated Oct. 12, 2018.

Peer at Tamu, "A syringe with a Needle Fills Another Syring", See video at 1.40 min, available at: https://www.youtube.com/watch?v=Ch1murqNz7M, Apr. 9, 2019, 3 pages.

\* cited by examiner

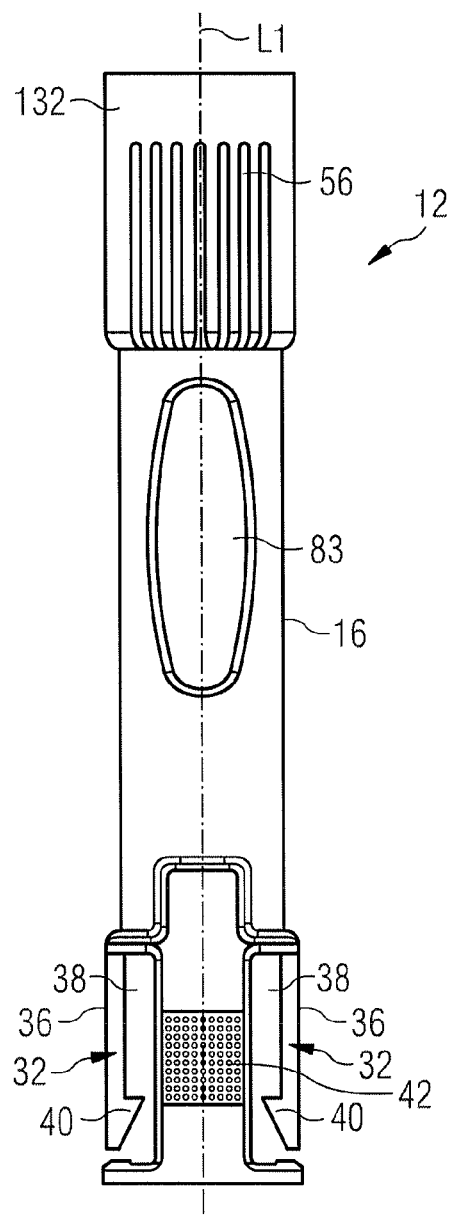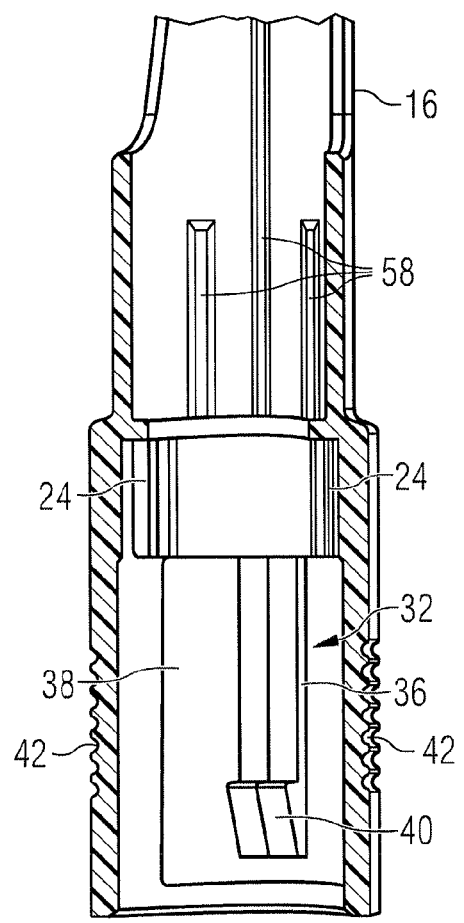

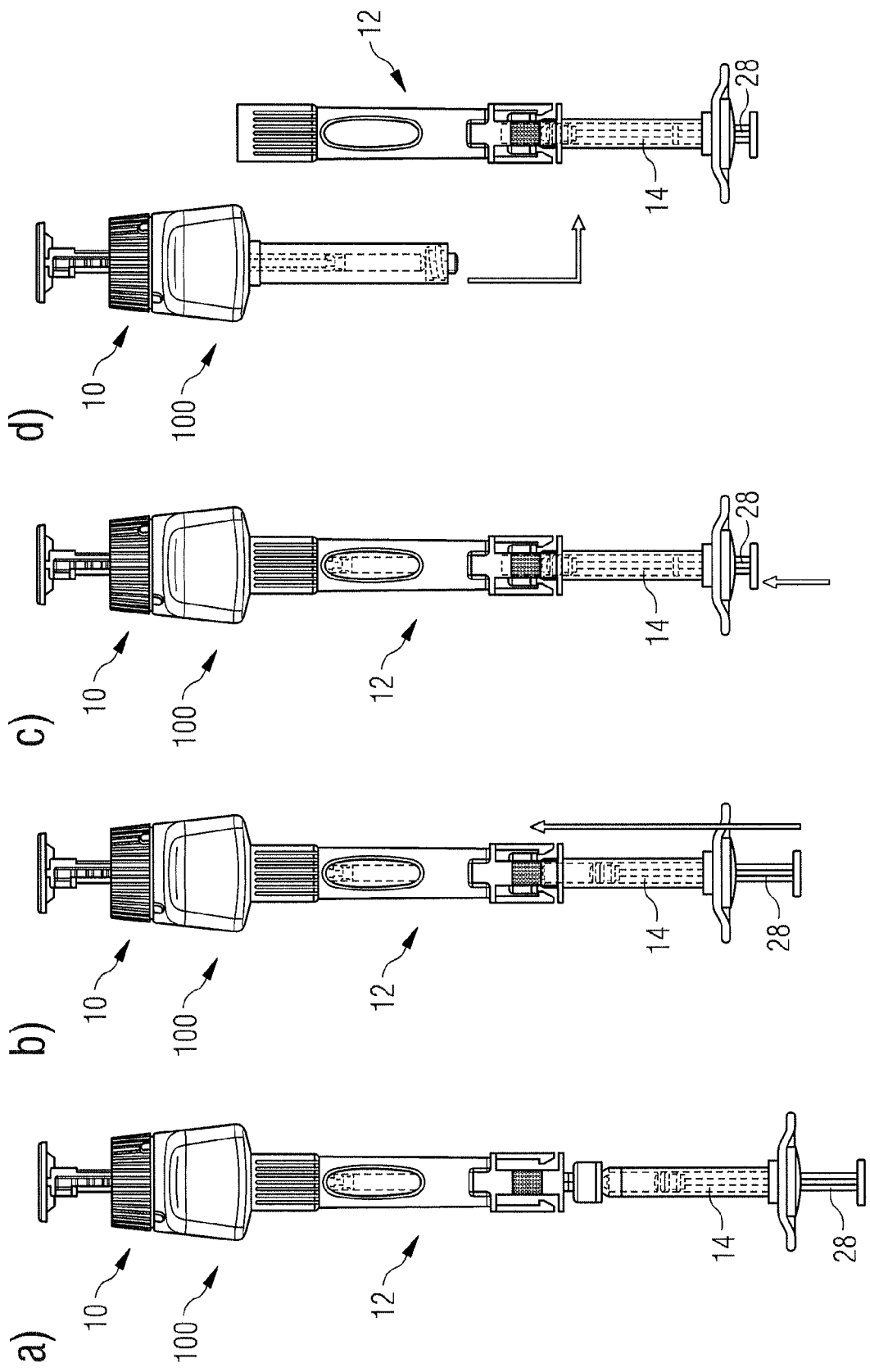

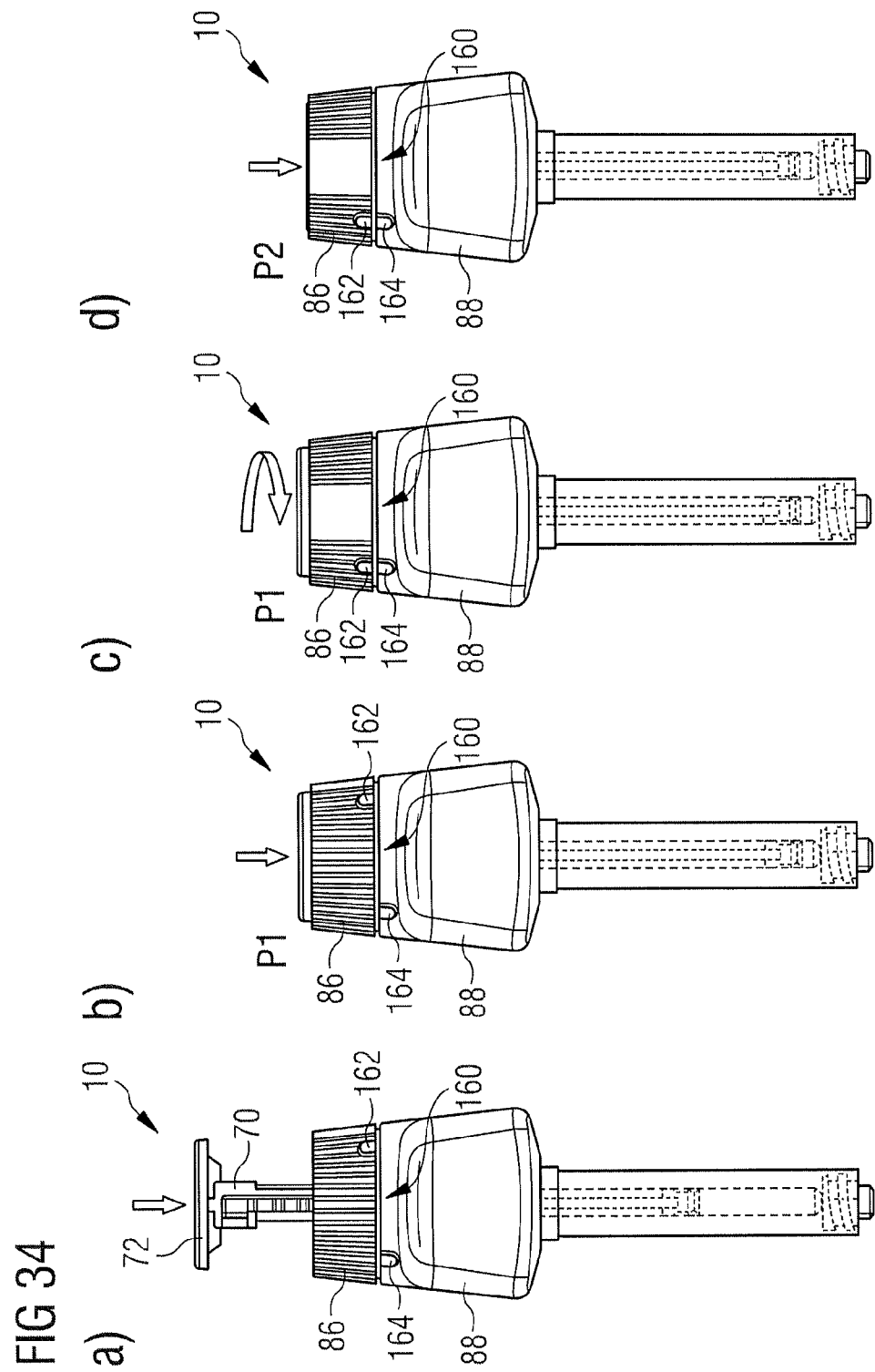

INJECTION DEVICE AND INJECTION SOLUTION TRANSFERRING SYSTEM

FIELD

The invention relates to an injection device, in particular a micro dose injection device such as, for example, an ophthalmic injection device for intraocular use. Further, the invention relates to an injection solution transferring system for transferring an injection solution from a syringe to an injection device of this kind.

BACKGROUND

Typically, an injection solution to be administered to a patient for medical treatment is stored within a syringe having a container for accommodating the injection solution and a plunger which is displaceable relative to the container in order to expel the injection solution from the container. In case the medical treatment plan for a patient provides for the administration of a dose of the injection solution which corresponds to the filling volume of the syringe or in case the dosage of the injection solution is of minor importance for the desired therapeutic effect, the injection solution may be administered to the patient directly from the syringe. However, in case the medical treatment plan for a patient requires the administration of a dose of the injection solution which differs from the filling volume of the syringe and/or in case an accurate dosage of the injection solution is necessary, the injection solution, prior to administration, may be transferred from the syringe to an injection device which finally is used to inject the desired dose of the injection solution into the patient.

US 2002/052578 A1 describes an injection device for injection of set doses of medicine from a cartridge. The injection device comprises a housing, a threaded piston rod which is linearly displaceable in the housing and a displaceable nut that moves relative to the housing and engages the thread of the piston rod so that the nut can screw along the thread of the piston rod. The displacement of the nut along the piston rod defines a quantity of medication to be injected by the injection device.

SUMMARY

The invention is directed at the object of providing an injection device which allows the accurate and reliable administration of a micro dose of an injection solution to a patient. Further, the invention is directed at the object of providing an injection solution transferring system for transferring an injection solution from a syringe to an injection device of this kind.

This object is addressed by an injection device and an injection solution transferring system as disclosed and described herein.

An injection device comprises an injection solution receptacle. The injection solution receptacle and the protective outer barrel can be made from any suitable material, or combination of materials, including a plastic material or from glass. Suitable plastic material comprises for example cycloolefin polymer or cycloolefin copolymer. An example of a glass material may be borosilicate glass. Preferably, the glass material is tungsten-free. In one embodiment the injection solution receptacle may be uncoated. Uncoated means that the injection solution receptacle does not contain any other material other than the material of which the injection solution receptacle is made of. Alternatively, the injection solution receptacle may comprise an internal coating. Internal coating means a coating on the inner side of the injection solution receptacle which is in contact with the injection solution. Examples of such an internal coating comprise silicone coating or a fluorocarbon film made from a modified ethylene-tetrafluoroethylene copolymer. The injection solution receptacle may be silicone free, or substantially silicone free, or may comprise a low level of silicone as lubricant. Preferably, the injection solution receptacle is made of a sterile plastic material. Preferably, the injection solution receptacle is made of a sterile plastic material. Preferably, the injection solution receptacle does not comprise an internal coating. In one embodiment, the injection solution receptacle may meet USP789.

The injection solution receptacle may be designed in the form of an inner injection solution receptacle which is contained within a protective outer barrel. An injection solution receptacle designed in the form of an inner injection solution receptacle may be formed integral with the protective outer barrel. In the region of its proximal end, the protective outer barrel may be provided with a flange element which may serve to connect the protective outer barrel and the inner injection solution receptacle to a housing of the injection device. For example, the housing of the injection device may comprise a suitably shaped and dimensioned receptacle for receiving the flange element and hence fastening the protective outer barrel and the inner injection solution receptacle to the housing.

A distal end of the injection solution receptacle of the injection device may be provided with a male part of a Luer taper which is adapted to interact with a female part of a Luer taper. The female part of a Luer taper may, for example, be provided on a connecting port of an adapter element of a filling adapter which may be used to connect the injection device to a syringe containing an injection solution to be transferred from the syringe to the injection solution receptacle of the injection device. By means of the Luer taper, a fluid-tight connection can be established between the distal end of the injection solution receptacle of the injection device and the adapter element of the filling adapter in a simple manner. The outer barrel of the injection device, in the region of its distal end, may be provided with a Luer thread which is adapted to interact with a complementary Luer thread provided at the second connecting port of the adapter element of the filling adapter, in particular in the region of its outer circumference. As a result, also a reliable connection between the outer barrel of the injection device and the adapter element of the filling adapter can be effected.

The injection device further comprises a plunger. The plunger may be made of polycarbonate. At least a portion of the plunger is slidably received within the injection solution receptacle. The plunger is displaceable relative to the injection solution receptacle in a distal direction along a longitudinal axis of the plunger in order to expel an injection solution contained in the injection solution receptacle from the injection solution receptacle. At its proximal end which may protrude from the injection solution receptacle in a proximal direction, the plunger may carry an actuation button which may be depressed by a user in order to displace the plunger relative to the injection solution receptacle in the distal direction along the longitudinal axis of the plunger. At its distal end, the plunger may be provided with a tip element which may be attached to a plunger rod. A coupling between the plunger rod and the tip element may be effected, for example, by the interaction of a tip barb provided at a distal end of the plunger rod with a barb receptacle of the tip element. Further, the tip element may be provided with a sealing element which, for example, may be provided in the region of an outer circumferential surface of the tip element and which sealingly interacts with an inner circumferential surface of the injection solution receptacle.

The injection device further comprises a first plunger stop mechanism which is adapted to stop a displacement of the plunger relative to the injection solution receptacle in the distal direction at a first dosing position. Further, the injection device comprises a second plunger stop mechanism which is adapted to stop a displacement of the plunger relative to the injection solution receptacle from the first dosing position in the distal direction at a second dosing position. The first and the second dosing position of the plunger are selected in such a manner that the plunger, upon being displaced relative to the injection solution receptacle between the first and the second dosing position is adapted to expel a desired dose of the injection solution contained in the injection solution receptacle from the injection solution receptacle.

After filling the injection solution receptacle with the injection solution to be administered to a patient, a user of the injection device can expel excess injection solution from the injection solution receptacle by displacing the plunger relative to the injection solution receptacle in the distal direction until the plunger reaches the first dosing position. Upon reaching the first dosing position, the first plunger stop mechanism stops further displacement of the plunger in the distal direction. Consequently, the user is prevented from expelling too much injection solution from the injection solution receptacle. The residual injection solution contained in the injection solution receptacle can then be administered to a patient by further displacing the plunger in the distal direction until the plunger reaches the second dosing position. Upon reaching the second dosing position, the second plunger stop mechanism stops further displacement of the plunger in the distal direction and hence prevents that too much injection solution is administered to the patient.

The injection device allows the accurate and reliable administration of a micro dose of an injection solution to a patient. Further, the injection device can easily and comfortably be handled by a user. The injection device therefore is particularly suitable for treating a paediatric patient. In particular, the injection device may be designed in the form of an ophthalmic injection device for intraocular use.

In one embodiment, the injection device is filled with a dosage volume (i.e. the volume of injection solution intended for delivery to the patient) of between about 1 µl to about 50 µl, preferably between about 10 µl to about 20 µl, of an injection solution. In a preferred embodiment, the injection device is filled with a dosage volume of 5 µl, or 10 µl, or 20 µl, or 30 µl of an injection solution.

The injection device may be filled with any injection solution, for example an injectable medicament. In one embodiment, the injection device is filled with an injectable medicament comprising an active ingredient suitable for the treatment of an ocular disease. Examples of such ocular diseases include retinopathy of prematurity, geographic atrophy, glaucoma, choroidal neovascularisation, age-related macular degeneration (both wet and dry forms), macular edema secondary to retinal vein occlusion (RVO) including both branch RVO (bRVO) and central RVO (cRVO), choroidal neovascularisation secondary to pathologic myopia (PM), diabetic macular edema (DME), diabetic retinopathy, retinitis pigmentosa, Leber's congenital aumaurosis, Bietti crystalline dystrophy, and proliferative retinopathy. In one embodiment, the medicament comprises a biologic active.

The biologic active may be an antibody (or fragment thereof), a non-antibody protein, nucleic acids for gene therapy or cellular material for cell therapy. In one embodiment, the medicament comprises a VEGF antagonist. Suitable VEGF antagonists include ranibizumab (Lucentis™), bevacizumab (Avastin™), brolucizumab (also known as RTH258), aflibercept (Eylea™, also known as VEGF-Trap Eye), conbercept (KH902 from Chengdu Kanghong Biotechnologies Co. Ltd, described as FP3 in WO2005/121176, the contents of which are hereby incorporated by reference) and the related glycoform KH906 or pazopanib (from GlaxoSmithKline).

In a preferred embodiment, the injection device is filled with 0.1 mg or 0.2 mg ranibizumab in 20 µl injection solution. In a most preferred embodiment, the injection device is filled with 20 µl of ranibizumab (0.2 mg) and used for the treatment of retinopathy of prematurity.

In a preferred embodiment of the injection device, the first plunger stop mechanism comprises a dosing element which is attached to the plunger and which is adapted to abut against a first dosing surface provided on a housing element. Alternatively or additionally thereto, the second plunger stop mechanism may comprise a dosing element which is attached to the plunger and which is adapted to abut against a second dosing surface provided on a housing element.

Preferably, the dosing element of the first and/or the second plunger stop mechanism is formed integral with the plunger. For example, the dosing element may be designed in the form of a rib which may protrude from a surface of an actuation button of the plunger in the direction of the inner solution receptacle. Basically, it is conceivable that the injection device comprises a first dosing element associated to the first plunger stop mechanism and a second dosing element associated to the second plunger stop mechanism. Preferably, however, the injection device comprises only one dosing element which is attached to the plunger and which is associated to both the first and the second plunger stop mechanism. A single dosing element may be adapted, upon movement of the plunger in the distal direction, to first abut against the first dosing surface when the plunger reaches the first dosing position and then, upon further movement of the plunger from the first dosing position in the distal direction, against the second dosing surface when the plunger reaches the second dosing position.

The first and the second dosing surface may be provided on different housing elements of the injection device. In a preferred embodiment of the injection device, the first and the second dosing surface, however, both are formed on a first housing element, i.e. on the same housing element of the injection device. The first and the second dosing surface preferably extend substantially parallel to each other, wherein the second dosing surface may be arranged parallel offset relative to the first dosing surface in the distal direction. A distance between the first and the second dosing surface in the distal direction may correspond to a desired travel distance of the plunger in the distal direction between the first and the second dosing position. Hence, by suitably arranging the first and the second dosing surface, the desired plunger displacement between the first and the second dosing position and hence the desired injection solution dose to be expelled from the injection solution receptacle upon displacing the plunger from the first to the second dosing position can be set. The first and the second dosing surface may extend substantially parallel to an abutting surface of the dosing element. For example, the first and the second dosing surface as well as the abutting surface of the dosing element may extend substantially perpendicular to the longitudinal axis of the plunger.

The first plunger stop mechanism may be designed in such a manner that it provides a resistance force that is adapted to stop the displacement of the plunger at the first dosing position, but that can be overcome, for example by increasing the actuation force acting on the plunger. In a particular preferred embodiment of the injection device, the first plunger stop mechanism, however, is adapted to provide a hard stop for the plunger, i.e. is adapted to prevent the plunger from being displaced relative to the injection solution receptacle from the first dosing position in the distal direction without damaging the first plunger stop mechanism. In particular in case the first plunger stop mechanism is designed as a hard stop for the plunger, the injection device preferably further comprises a plunger releasing mechanism which is adapted to deactivate the first plunger stop mechanism in order to release the plunger and to thus allow a displacement of the plunger relative to the injection solution receptacle from the first dosing position in the distal direction, i.e. in the direction of the second dosing position.

Also the second plunger stop mechanism may be designed in such a manner that it provides a resistance force that is adapted to stop the displacement of the plunger at the second dosing position, but that can be overcome, for example by increasing the actuation force acting on the plunger. In a particular preferred embodiment, the second plunger stop mechanism, however, is adapted to provide a hard stop for the plunger, i.e. is adapted to prevent the plunger from being displaced relative to the injection solution receptacle from the second dosing position in the distal direction without damaging the second plunger stop mechanism. The dose of the injection solution to be administered to a patient can then be set in a particularly accurate manner.

Preferably, the plunger releasing mechanism is adapted to allow a movement of at least one of the dosing element and the first dosing surface in order to disengage the dosing element from the first dosing surface. The movement of the dosing element and/or the first dosing surface may be manually induced by a user of the injection device. In a particular preferred embodiment of the injection device, it is sufficient for a user to move only the first dosing surface for disengaging the dosing element from the first dosing surface. As a result, it is not necessary for the user to induce a movement of the plunger for activating the plunger releasing mechanism. For example, only the housing element carrying the first dosing surface may be moved for activating the plunger releasing mechanism, whereas the plunger may remain in its position, which simplifies the use of the injection device.

The plunger releasing mechanism may be adapted to allow a rotational movement of at least one of the dosing element and the first dosing surface in order to disengage the dosing element from the first dosing surface. For example, the plunger releasing mechanism may be activatable by a manually induced rotation of the plunger and/or the first dosing surface. In particular, the plunger releasing mechanism may be adapted to allow a rotational movement of the housing element carrying the first dosing surface for activating the plunger releasing mechanism. The actuation of a rotational movement of the plunger and/or the first dosing surface and in particular of only the first dosing surface can easily be distinguished by a user from the pressing actuation of the plunger so as to move the plunger in the distal direction. As a result, the use of the injection device is further simplified.

In a preferred embodiment of the injection device, the first and the second dosing surface are arranged offset relative to each other, for example on different or the same housing element(s), in a circumferential direction of the plunger. The plunger releasing mechanism then may be adapted to displace the first and the second dosing surface in the circumferential direction of the plunger, in order to disengage the dosing element from the first dosing surface and to simultaneously align the second dosing surface with the dosing element, such that the dosing element abuts against the second dosing surface, when the plunger, upon being displaced relative to the injection solution receptacle from the first dosing position in the distal direction, reaches the second dosing position. Such a design of the plunger releasing mechanism allows a particularly simple and reliable handling of the injection device.

Preferably, the first and the second dosing surface are formed on the first housing element which is rotatable relative to the plunger. In case the first and the second dosing surface are arranged offset relative to each other on the first housing element in a circumferential direction of the plunger, disengagement of the dosing element from the first dosing surface and simultaneous arrangement of the second dosing surface in a position wherein the second dosing surface is ready for engagement with the dosing element, when the plunger, upon being displaced from the first dosing position in the distal direction, reaches the second dosing position can easily be achieved by simply rotating the first housing element by a suitable rotation a mount.

The second dosing surface may be defined by a bottom surface of a recess formed in the first dosing surface. Preferably, the recess is designed, i.e. shaped and dimensioned, so as to allow the dosing element to be received in the recess. When the plunger is arranged in its first dosing position and the dosing element abuts against the first dosing surface, the recess defined in the first dosing surface, via a rotational movement of the first housing element, can be brought into alignment with the dosing element. As a result, the dosing element is disengaged from the first dosing surface and the plunger can further be displaced in the distal direction until the dosing element is received in the recess and the abutting surface formed on the dosing element abuts against the second dosing surface defined by the bottom surface of the recess. A depth of the recess which defines the distance between the first and the second dosing surface in the distal direction may correspond to the desired travel distance of the plunger in the distal direction between the first and the second dosing position.

The first housing element which carries the first and the second dosing surface, in particular in the region of an outer surface, may be provided with a gripping structure. For example, the gripping structure may be designed in the form of a gripping rib array with individual gripping ribs extending, in dependence on the shape of the outer surface of the first housing element, substantially in a direction along the longitudinal axis of the plunger. The gripping structure simplifies the handling of the plunger releasing mechanism.

Preferably, the plunger releasing mechanism comprises a marker system which is adapted to indicate an activation of the plunger releasing mechanism. The marker system may, for example, comprise a first marker element which is provided on the first housing element which carries the first and the second dosing surface, for example in the region of an outer surface thereof. The marker system may further comprise a second marker element which is provided on a second housing element of the injection device, in particular in the region of an outer surface thereof. The first and the second marker element may be arranged on the first and the second housing element in such a position that they are positioned offset relative to each other, for example in a circumferential direction of the plunger, when the plunger releasing mechanism is not activated, but positioned in alignment with each other, when the plunger releasing mechanism is activated. The marker system provides a user with guidance information on how to activate the plunger release mechanism and hence simplifies the handling of the injection device.

The injection device preferably further comprises an activation mechanism which is adapted to prevent an activation of the plunger releasing mechanism unless the plunger is arranged at the first dosing position and which is adapted to allow an activation of the plunger releasing mechanism when the plunger is arranged at the first dosing position. The activation mechanism may be adapted to prevent a movement of the dosing element and/or the first dosing surface relative to each other unless the plunger is arranged at the first dosing position. In particular, the activation mechanism may be adapted to prevent a rotation of the first housing element carrying the first and the second dosing surface relative to the plunger carrying the dosing element unless the plunger is arranged at the first dosing position.

In a preferred embodiment of the injection device, the activation mechanism comprises a guiding channel which is provided on a circumferential surface of the plunger, which extends along the longitudinal axis of the plunger and which receives a guiding element provided on a housing element in such a manner that the guiding channel, upon displacement of the plunger relative to the injection solution receptacle, is displaced relative to the guiding element. An interaction between the guiding element and opposing side surfaces of the guiding channel may prevent a rotation of the plunger and the housing element relative to each other. When the activation mechanism comprises a guiding channel extending along the longitudinal axis of the plunger and a corresponding guiding element, the activation mechanism fulfills the double function to provide for a guided displacement of the plunger in the direction of its longitudinal axis on the one hand and to simultaneously prevent an unintentional deactivation of the first plunger stop mechanism when the plunger is not arranged at the first dosing position. The guiding element may be provided on the first housing element which carries the first dosing surface and preferably also the second dosing surface.

The activation mechanism may further comprise an activation channel which branches off from the guiding channel. For example, the activation channel may extend in a circumferential direction of the plunger substantially perpendicular to the guiding channel. The activation channel preferably is adapted to receive the guiding element when the plunger is arranged at the first dosing position and the first housing element which carries the guiding element and preferably also the first and the second dosing surface is rotated relative to the plunger. With such a design of the activation mechanism, the first dosing position of the plunger is defined by the position of the activation channel along the longitudinal axis of the plunger.

The first and the second dosing surface may be formed on the first housing element which is rotatable relative to the plunger. In case the first and the second dosing surface are arranged offset relative to each other on the first housing element in a circumferential direction of the plunger, disengagement of the dosing element from the first dosing surface and simultaneous arrangement of the second dosing surface in a position wherein the second dosing surface is ready for engagement with the dosing element, when the plunger, upon being displaced from the first dosing position in the distal direction, reaches the second dosing position can easily be achieved by simply rotating the first housing element by a suitable rotation amount.

The second dosing surface may be defined by a bottom surface of a recess formed in the first dosing surface. Preferably, the recess is designed, i.e. shaped and dimensioned, so as to allow the dosing element to be received in the recess. When the plunger is arranged in its first dosing position and the dosing element abuts against the first dosing surface, the recess defined in the first dosing surface, via a rotational movement of the first housing element, can be brought into alignment with the dosing element. As a result, the dosing element is disengaged from the first dosing surface and the plunger can further be displaced in the distal direction until the dosing element is received in the recess and the abutting surface formed on the dosing element abuts against the second dosing surface defined by the bottom surface of the recess.

The plunger release mechanism may further comprise a locking arrangement which is adapted to lock the first dosing surface in its position relative to the dosing element after the first dosing surface has been moved relative to the dosing element in order to become disengaged from the dosing element. The locking arrangement thus allows the plunger release mechanism to be used only once for deactivating the first plunger stop mechanism. As a result, reuse of the injection device is reliably prevented.

The locking arrangement may comprise a resilient locking clip which is adapted to be resiliently urged out of a rest position by the interaction with a locking element when the first dosing surface is moved relative to the dosing element so as to become disengaged from the dosing element. For example, the resilient locking clip may be provided on the second housing element, whereas the locking element may be provided on the first housing element which carries the first dosing surface and optionally also the second dosing surface. The resilient locking clip then may be resiliently deformed when the first housing element is rotated relative to the second housing element. The locking clip preferably further is adapted to deform back into its rest position after completion of the movement of the first dosing surface and to interact with the locking element so as to lock the first dosing surface in its position relative to the dosing element. In particular, the locking clip may interact with the locking element so as to prevent a counter rotation of the first housing element relative to the second housing element and the plunger, after the first housing element has been rotated once in order to disengage the first dosing surface from the dosing element and to align the second dosing surface with the dosing element.

The injection device may further comprise a limiting mechanism which is adapted to limit a movement of the dosing element and/or both the first dosing surface and the second dosing surface for disengaging the dosing element from the first dosing surface and for aligning the dosing element with the second dosing surface. The limiting mechanism prevents a user of the injection device from moving the dosing element and the first and the second dosing surface relative to each other in an excessive manner. Further, the limiting mechanism provides an haptic feedback to the user that the dosing element is properly disengaged from the first dosing surface and aligned with the second dosing surface, i.e. that the first plunger stop mechanism has been deactivated.

The limiting mechanism may in particular comprise a first limiting element which is provided on the first housing element carrying the first and the second dosing surface. Further, the limiting mechanism may comprise a second limiting element which is provided on a second housing element, the second housing element being adapted to remain stationary when the first housing element is moved, in particular rotated, for deactivating the first plunger stop mechanism. The first limiting element may be adapted to abut against the second limiting element when the dosing element is disengaged from the first dosing surface and aligned with the second dosing surface.

In case the injection device comprises an above-described activation mechanism with an activation channel and a guiding element formed on the first housing element which also carries the first and the second dosing surface, the movement of the first dosing surface relative to the dosing element attached to the plunger may also be limited by an interaction between the guiding element and an end face of the activation channel which may act as an abutting surface for the guiding element when the first housing element, after being rotated relative to the plunger, has reached a position wherein the dosing element is disengaged from the first dosing surface and aligned with the second dosing surface.

The injection device may further comprise a first drag mechanism adapted to exert a retaining force which retains the plunger in its current position relative to the injection solution receptacle. The first drag mechanism thus prevents an unintentional displacement of the plunger relative to the injection solution receptacle—in other words, due to the presence of the first drag mechanism, active manual actuation, for example by the application of a pressing force, is necessary for displacing the plunger relative to the injection solution receptacle. The first drag mechanism may comprise a resilient drag element which may, for example, be provided on the second housing element. The resilient drag element may be adapted to exert a resilient retaining force on the plunger, i.e. the resilient drag element may be resiliently urged out of a rest position into a biasing position by an interaction with the plunger and, due to its resiliency, may apply a resilient reaction force on the plunger which retains the plunger in its current position. The resilient drag element may in particular interact with a drag rib which is provided on the outer circumferential surface of the plunger and which extends substantially parallel to the longitudinal axis of the plunger.

Alternatively or additionally thereto, the injection device may also comprise a second drag mechanism adapted to exert a retaining force which retains the first housing element in its current position, i.e. which retains the first housing element in its position relative to the second housing element. The second drag mechanism thus prevents an unintentional displacement of the first housing element relative to the second housing element and hence an unintentional deactivation of the first plunger stop mechanism. The second drag mechanism may comprise a friction element which is provided on the first limiting element of the limiting mechanism and which is adapted to interact with a retaining element of the second housing element.

The injection device may further comprise a plunger positioning mechanism which is adapted to prevent a displacement of the plunger relative to the injection solution receptacle from a proximal end position in a proximal direction. The plunger positioning mechanism may, for example, comprise a distal end face of the guiding channel which is provided in the circumferential surface of the plunger. An interaction between the distal end face of the guiding channel and the guiding element received therein then may define the proximal end position of the plunger.

The injection device may be pre-filled with a compound, via a pre-filled syringe (14), a vial, or other reservoir.

In one embodiment, the injection device (whether pre-filled or not) is sterilized and provided in a sealed package. In one embodiment, the injection device is pre-filled with a suitable injection solution and terminally sterilized. Such a terminal sterilization step may comprise known techniques such as ethylene oxide sterilization or hydrogen peroxide sterilization.

BRIEF DESCRIPTION OF THE SEVERAL VIEWS OF THE DRAWING

A preferred embodiment of the invention now will be described in greater detail with reference to the appended schematic drawings, wherein:

FIGS. 4 and 5 show detailed three-dimensional views of a hollow sleeve of the filling adapter, FIGS. 33a to 33d show the use of the injection solution transferring system upon filling the injection device with an injection solution from a syringe, and FIGS. 34a to 34d show the use of the injection device upon administering an injection solution to a patient.

DETAILED DESCRIPTION OF THE INVENTION

Figure 1:
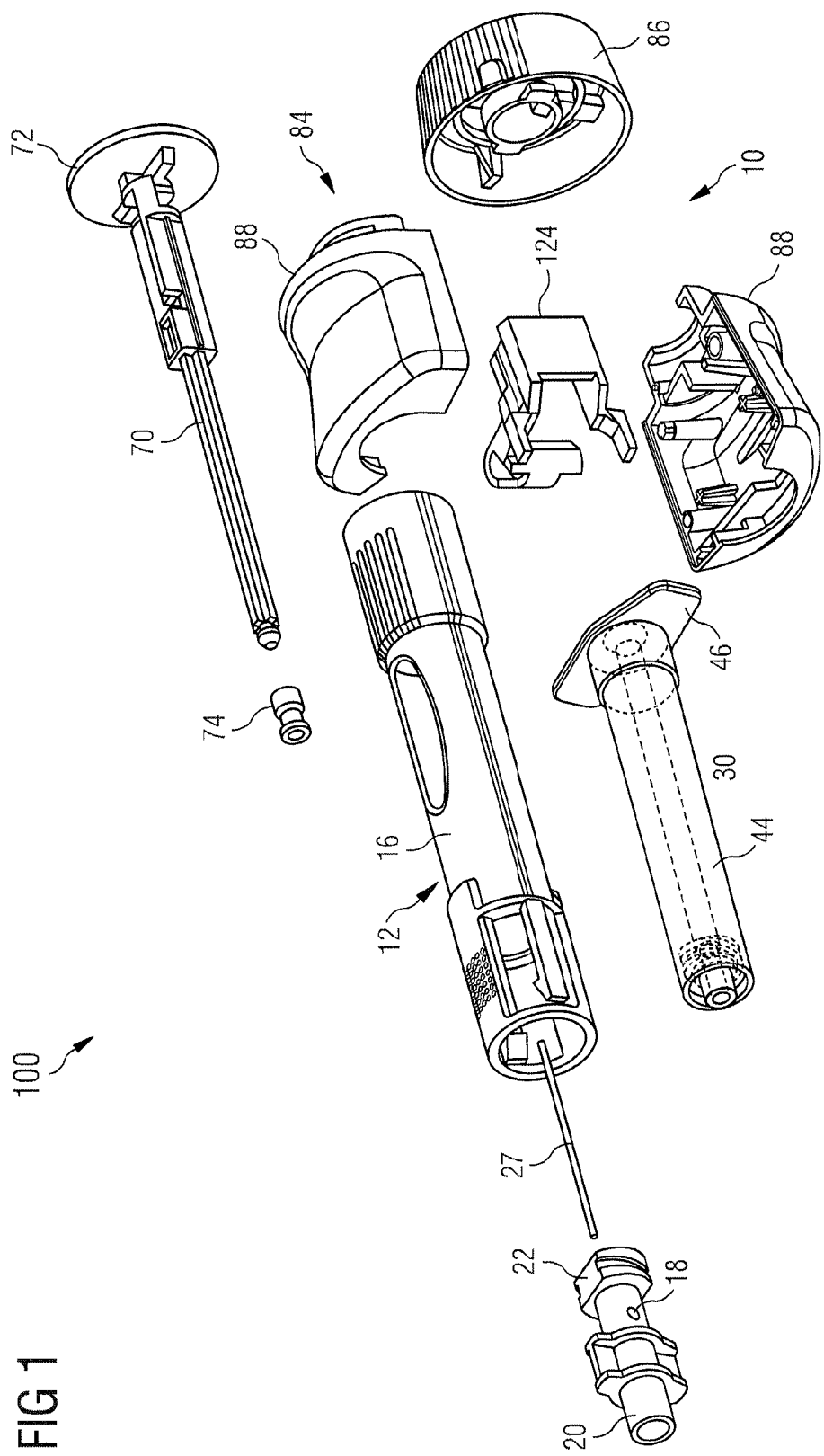
FIG. 1 shows an exploded view of an injection solution transferring system which comprises a filling adapter and injection device.
Figure 2:
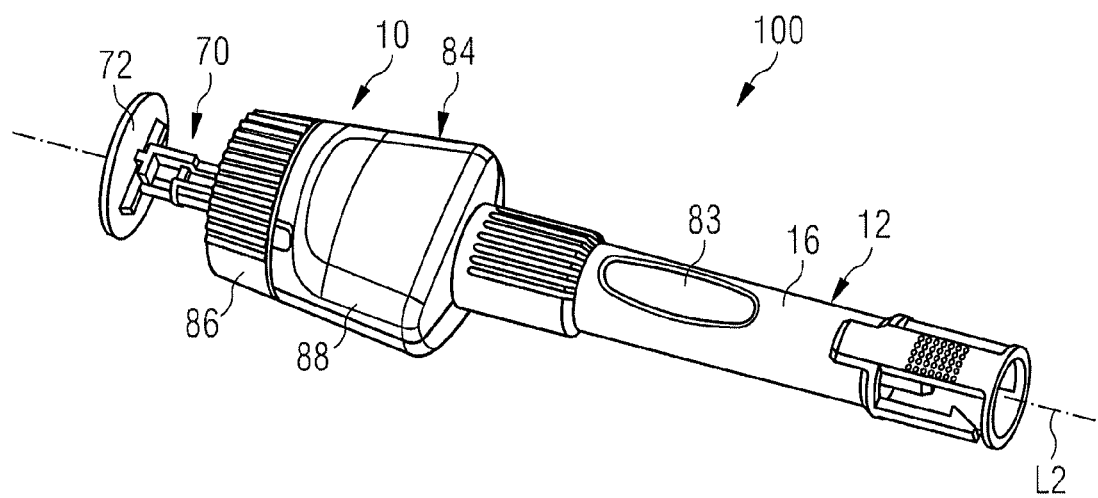
FIG. 2 shows a three-dimensional view of the filling adapter and the injection device in a connected state.

FIGS. 1 and 2 show an injection solution transferring system 100 which comprises an injection device 10 and a filling adapter 12. The filling adapter 12 serves to connect a syringe 14 containing an injection solution to the injection device 10 for filling the injection device 10 with the injection solution from the syringe 14 as shown in FIGS. 33a to 33d and as will be described further below. The syringe 14 is designed in the form of a pre-filled syringe 14 which contains an injection solution for intraocular use.

The filling adapter 12 comprises a hollow sleeve 16 which is shown in greater detail in FIGS. 4 and 5. The hollow sleeve 16 made of a coloured plastic material, for example Polycarbonate/Acrylnitril Butadien Styrol (PC-ABS) and is provided with an inner lumen which is dimensioned so as to allow the insertion of at least a distal portion of the syringe 14 at one end and of at least a distal portion of the injection device 10 at an opposing end. In the exemplary embodiment of a filling adapter 12 shown in the drawings, the hollow sleeve 16 has a substantially circular hollow cylindrical shape and the lumen extending therethrough has a substantially circular cross-sectional shape.

The filling adapter 12 further comprises an adapter element 18 which is accommodated within the hollow sleeve 16 and which comprises a first connecting port 20 and a second connecting port 22. The adapter element 18 may, for example, be made of polycarbonate and is shown in greater detail in FIGS. 6 to 10. As shown in particular in FIG. 8, the adapter element 18 is provided with two retention shoulders 23 which protrude from an outer circumferential surface of the adapter element 18 in opposing directions. Each retention shoulder 23 interacts with a pair of complementary crush ribs 24 protruding from an inner circumferential surface of the hollow sleeve 16 in order to fix the adapter element 18 in its position within the hollow sleeve 16. The retention shoulders 23 and the complementary crush ribs 24 create an interference fit so as to reliably fix the adapter element 18 in its position within the hollow sleeve 16.

The first connecting port 20 of the adapter element 18 is adapted to be connected to the syringe 14, i.e. a distal end of the syringe 14, when the filling adapter 12 is connected to the syringe 14 as shown in FIGS. 33a to 33c. As becomes apparent in particular from FIG. 10, the first connecting port 20 of the adapter element 18 forms a female Luer taper 25 which is adapted to interact with a male Luer taper provided at the distal end of the syringe 14 in order to establish a fluid-tight connection between the syringe 14 and the adapter element 18. The second connecting port 22 of the adapter element 18 is adapted to be connected to the injection device 10.

Figure 9:
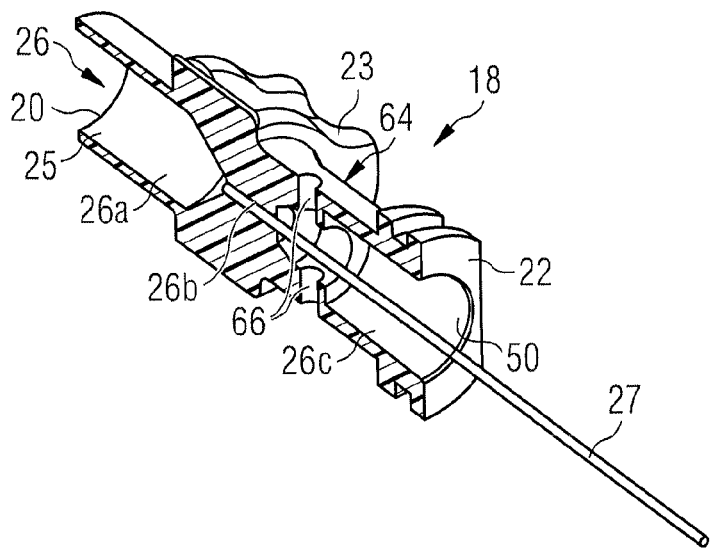
FIG. 9 shows a three-dimensional longitudinal cut view of the adapter element and a cannula of the filling adapter.
Figure 10:
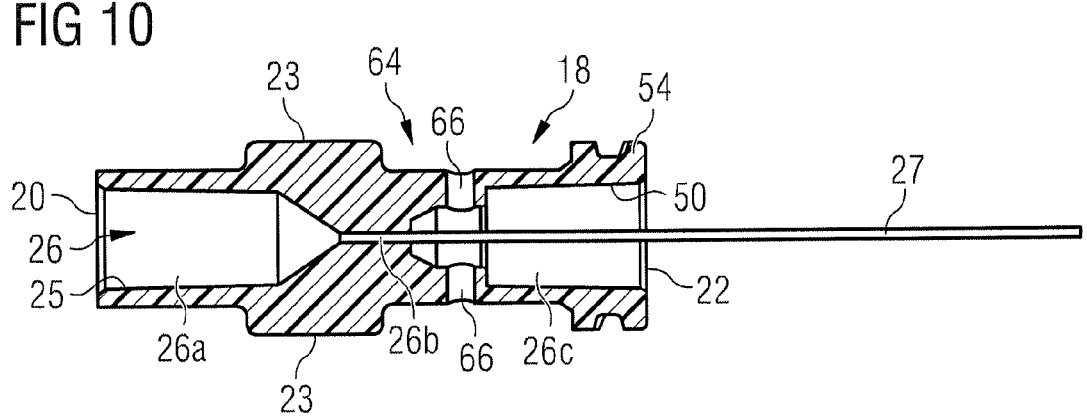
FIG. 10 shows a longitudinal section of the adapter element and the cannula of the filling adapter.

The adapter element 18 is provided with a through-opening 26 extending therethrough in a direction substantially parallel to a longitudinal axis L1 of the filling adapter 12, see in particular FIG. 10. A cannula 27 protrudes from the second connecting port 22 of the adapter element 18 and is arranged in fluid communication with the through-opening 26 extending through the adapter element 18, see in particular FIGS. 9 and 10. The cannula 27 is made of stainless steel. The hollow sleeve 16 of the filling adapter 12, however, extends beyond a distal tip of the cannula 27. As a result, a user is protected from the cannula 27 during handling of the filling adapter 12.

The adapter element 18 serves to establish a fluid connection between the syringe 14 and the injection device 10, i.e. when the syringe 14 is connected to the first connecting port 20 of the adapter element 18 and the injection device 10 is connected to the second connecting port 22 of the adapter element 18 as shown in FIG. 33a, injection solution contained in the syringe 14 may be transferred into the injection device 10 by manually pushing a plunger 28 of the syringe 14 as shown in FIGS. 33b and 33c so as to expel the injection solution from the distal end of the syringe 14 into the through-opening 26 provided in the adapter element 18 and further via the cannula 27 into an injection solution receptacle 30 of the injection device 10.

As becomes apparent in particular from FIGS. 4 and 5, the hollow sleeve 16 of the filling adapter 12, in the region of a first end which faces the syringe 14 when the syringe 14 is brought into engagement with the first connecting port 22 of the adapter element 18, the hollow sleeve 16 comprises at least one resilient clip 32 which is adapted to engage with a collar 34 of the syringe 14 when the syringe 14 is brought into engagement with the first connecting port 20 of the adapter element 18, see FIGS. 33a and 33b. In the embodiment of a hollow sleeve 16 shown in the drawings, the hollow sleeve 16 is provided with two resilient clips 32. Each resilient clip 32 comprises an arm 36 which extends in a recess 38 provided in the hollow sleeve 16 substantially parallel to the longitudinal axis L1 of the filling adapter 12 in the direction of the first end of the hollow sleeve 16. A latching nose 40 protrudes from an inner surface of the arm 36 in the region of a free end of the arm 36.

When the syringe 14 is brought into engagement with the first connecting port 20, due to the interaction with the collar 34 of the syringe 14, the resilient clip 32 is bent outwards. However, as soon as the syringe 14 has reached its final position with respect to the adapter element 18, i.e. when the distal tip of the syringe 14 is connected to the first connecting port 20 of the adapter element 18 and the syringe 14 assumes the position relative to the hollow sleeve 16 which is shown in FIG. 33b, the resilient clip 32 resumes its original position substantially parallel to the longitudinal axis L1 of the filling adapter 12 such that the latching nose 40 comes into engagement with an end face of the collar 34 of the syringe 14. As a result, the syringe 14 is firmly connected to the hollow sleeve 16.

In the region of its first end, the hollow sleeve 16 at its outer circumferential surface is provided with two first gripping structures 42 each of which is designed in the form of a nub array. The first gripping structure simplifies the handling of the filling adapter 12 during connecting the syringe 14 to the filling adapter 12. Further, the hollow sleeve 16, in the region of its first end and the region of a second end which faces the injection device 10 when the injection device 10 is brought into engagement with the second connecting port 22 of the adapter element 18, has an outer diameter which is larger than an outer diameter of the hollow sleeve 16 in an intermediate section arranged between the first and the second end. Such a design of the hollow sleeve 16 further simplifies the gripping and thus the handling of the filling adapter 12.

Figure 3:
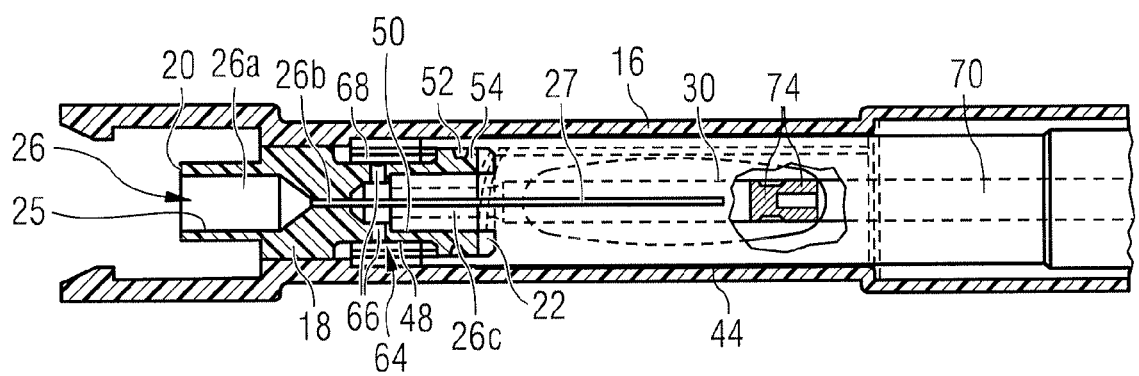
FIG. 3 shows a longitudinal section of the filling adapter being connected to the injection device.
Figure 6:
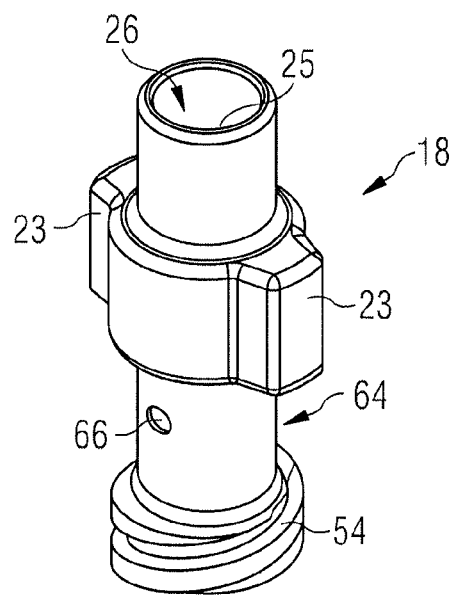
FIGS. 6 and 7 show detailed three-dimensional views of an adapter element of the filling adapter.
Figure 7:
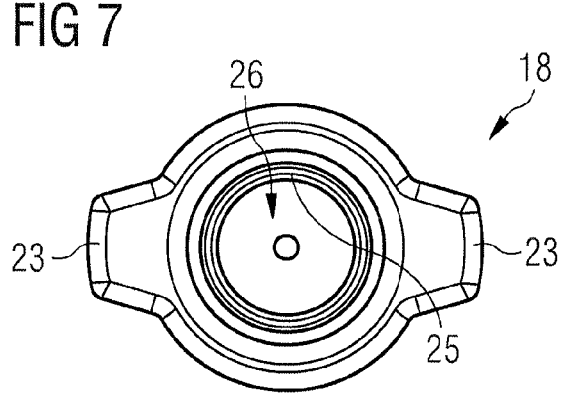
Figure 11:
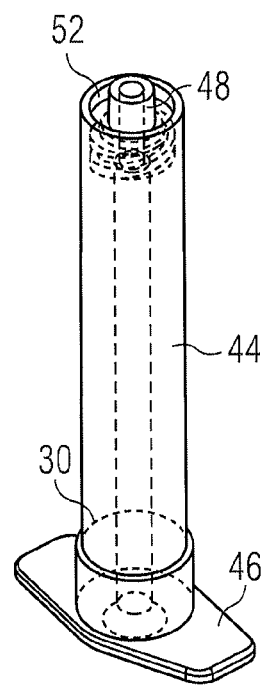
FIG. 11 shows a detailed view of an injection solution receptacle of the injection device.

As shown in in FIG. 11, the injection solution receptacle 30 of the injection device 10 is designed in the form of an inner injection solution receptacle 30 which is contained within a protective outer barrel 44. The inner injection solution receptacle 30 and the protective outer barrel 44 are formed integral with each other and are made of a sterile plastic material. In the region of its proximal end, the protective outer barrel 44 is provided with a flange element 46. A distal end of the injection solution receptacle 30 is provided with a male Luer taper 48 which interacts with a female Luer taper 50 provided on the second connecting port 22 of the adapter element 18 of the filling adapter 12 when the filling adapter 12 is connected to the injection device 10 as shown in FIGS. 2 and 3. By means of the Luer tapers 48, 50, a fluid-tight connection can be established between the distal end of the injection solution receptacle 30 and the adapter element 18 of the filling adapter 12.

As further becomes apparent from FIG. 11, the outer barrel 44 of the injection device 10, in the region of its distal end, is provided with a Luer thread 52. The Luer thread 52 interacts with a complementary Luer thread 54 provided at an outer circumference of the second connecting port 22 of the adapter element 18, see FIGS. 6 and 8 to 10, when the filling adapter 12 is connected to the injection device 10 as shown in FIGS. 2 and 3. As a result, also a reliable connection between the outer barrel 44 of the injection device 10 and the adapter element 18 of the filling adapter 12 can be effected.

In order to simplify the handling of the filling adapter 12 during bringing the injection device 10 into engagement with the second connecting port 22 of the adapter element 18, the hollow sleeve 18, in the region of a second end which faces the injection device 10 when the injection device 10 is brought into engagement with the second connecting port 22 of the adapter element 18, at its outer circumferential surface is provided with a second gripping structure 56. The second gripping structure 56 is designed in the form of two gripping rib arrays with individual gripping ribs extending substantially parallel to the longitudinal axis L1 of the filling adapter 12.

Figure 15:
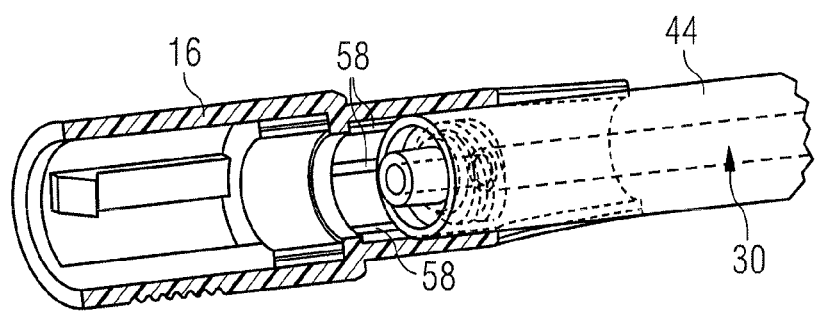
FIG. 15 shows the interaction between the guiding rib of the hollow sleeve with the injection solution receptacle of the injection device.

Further, as shown in FIG. 15, the hollow sleeve 16 is provided with longitudinal guiding ribs 58 which protrude from the inner circumferential surface of the hollow sleeve 16 and which extend substantially parallel to the longitudinal axis L1 of the filling adapter 12. The guiding ribs 58 serve to guide the injection device 10 into engagement with the second connecting port 22. The guiding function of the guiding ribs 58 prevents the cannula 27 from contacting the injection solution receptacle 30 of the injection device 10 upon connecting the filling adapter 12 to the injection device 10. The hollow sleeve 16 and the longitudinal guiding ribs 58 are designed, i.e. shaped and dimensioned, in such a manner that a close sliding fit is generated between the guiding ribs 58 and an outer surface of the outer barrel 54 of the injection device 10.

Turning back to FIGS. 9 and 10, the through-opening 26 extending through the adapter element 18 comprises an inlet section 26a which is arranged adjacent to the first connecting port 20. In use of the filling adapter 12, injection solution expelled from the syringe 14 thus enters the through-opening 26 via its inlet section 26a which has a flow cross-section which decreases in a direction of flow of the injection solution expelled from the syringe 14. Further, the through-opening 26 comprises an intermediate section 26b which, in the direction of flow of the injection solution expelled from the syringe 14 during use of the filling adapter 12, is arranged downstream of the inlet section 26a. The intermediate section 26b of the through-opening 26 has a substantially constant flow cross-section which substantially corresponds to the smallest flow cross-section of the inlet section 26a adjacent to the intermediate section 26b. Finally, the through-opening 26 comprises a receiving section 26c which, in the direction of flow of the injection solution expelled from the syringe 14 during use of the filling adapter 12, is arranged downstream of the intermediate section 26b, i.e. adjacent to the second connecting port 22. The receiving section 26c has a flow cross-section that is larger than the flow cross-section of the intermediate section 26b.

As further becomes apparent from FIGS. 9 and 10, the cannula 27 extends into at least a portion of the intermediate section 26b of the through-opening 26 so that the intermediate section 26b of the through-opening 26 or a portion thereof defines a cannula receiving bore of the adapter element 18 wherein a proximal end of the cannula 27 is fixed. The cannula 27 is received in the cannula receiving bore with a close slide fit. In addition, the cannula 27 is provided with bevelled ends. This design of the cannula 27 and the cannula receiving bore minimizes the generation of wear particles upon attaching the cannula 27 in the cannula receiving bore. The final bonding between the adapter element 18 and the cannula 27 is effected by means of a UV-cured glue. The cannula 27 extends from the intermediate section 26b of the through-opening 26, through the receiving section 26c of the through-opening 26 and the second connecting port 22 so as to protrude from the second connecting port 22. The receiving section 26c of the through-opening 26, the second connecting port 22 and the hollow sleeve 16 of the filling adapter 12 define a concentric arrangement around the cannula 27, see in particular FIG. 3.

Figure 8:
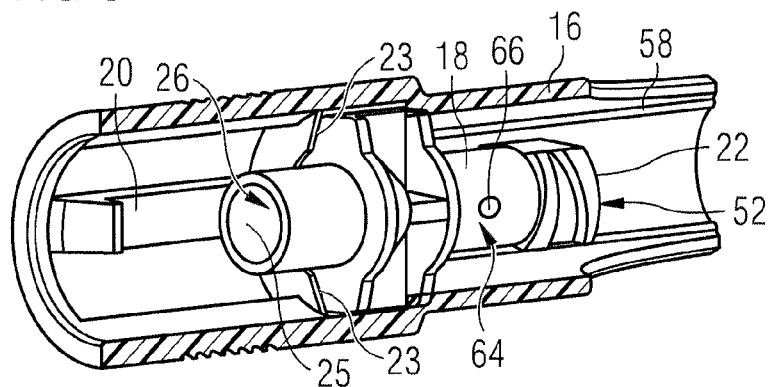
FIG. 8 shows the arrangement of the adapter element in the hollow sleeve of the filling adapter.

As shown in particular in FIG. 8, the adapter element 18 is provided with two retention shoulders 60 which protrude from an outer circumferential surface of the adapter element 18 in opposing directions in the region of the inlet section 26a and the intermediate section 26b of the through-opening 26 extending through the adapter element 18.

When the filling adapter 12 is connected to the injection device 10, the cannula 27 extends into the injection solution receptacle 30 of the injection device 10, i.e. a distal tip of the cannula 27 is arranged at a distance from the distal end of the injection solution receptacle 30 within the interior of the injection solution receptacle 30, see in particular FIG. 3. As a result, upon transferring injection solution from the syringe 14 to the injection device 10, injection solution exiting the syringe 14, via the cannula 27, is supplied to the injection solution receptacle 30 of the injection device 10 not in the region of the distal end of the injection solution receptacle 30, but at a position arranged at a distance from the distal end of the injection solution receptacle 30 within the interior of the injection solution receptacle 30.

By simply holding the filling adapter 12 and the injection device 10 in an upright position with the longitudinal axis L1 of the filling adapter 12 and a longitudinal axis L2 of the injection device 10 being oriented substantially vertically and with the distal end of the injection device 10 facing downwards as shown in FIGS. 33a to 33c, a gravity-driven flow of the injection solution from the distal tip of the cannula 27 downwards in a direction of the distal end of the injection solution receptacle 30 and further in the direction of the adapter element 18 can be induced. A part of the injection solution which is expelled from the distal tip of the cannula 27 and which in a gravity-driven manner flows back in the direction of the adapter element 18 is received in the receiving section 26c of the opening 26 provided in the adapter element 18. Gas bubbles which are entrapped within the injection solution and hence transferred from the syringe 14 to the injection solution receptacle 30 together with the liquid phase of the injection solution are entrained with this gravity-driven flow and, due to the higher specific density of the liquid phase of the injection solution, are forced in the direction of the distal end of the injection solution receptacle 30 and further in the direction of the adapter element 18.

Finally, the adapter element 18 is provided with a venting device 64 which is adapted to vent gas introduced from the syringe 14 into the injection device 10, i.e. the injection solution receptacle 30 of the injection device 10, via the through-opening 26 and the cannula 27 into the ambient. The venting device thus allows entrapped gas bubbles, in particular air bubbles, that are conveyed from the distal tip of the cannula 27 back to the adapter element 18 by the above described gravity-driven flow of the injection solution to be expelled into the ambient. The filling adapter 12 thus allows a gas free filling of the injection device 10 with the injection solution. As a result, manually expelling entrapped gas from the syringe 14 prior to connecting the syringe 14 to the filling adapter 12 can be dispensed with. Furthermore, an accurate and reliable preparation of a desired dose of the injection solution within the injection device 10 is made possible.

The venting device 64 comprises two radial bores 66 connecting the through-opening 26 extending through the adapter element 18 to the ambient. In particular, the radial bores 66 connect the receiving section 26c of the through-opening 26 to an outer circumferential surface of the adapter element 18 and hence to the ambient. In the embodiment of a filling adapter 18 shown in the drawings, the radial bores 66 of the venting device 64 extend coaxially from an outer circumferential surface of the adapter element 18 to the receiving section 26c of the through-opening 26 so as to connect the receiving section 26c of the through-opening 26 to the ambient. In order to ensure that gas bubbles entrapped in the injection solution can be vented to the ambient as desired without expelling a substantial amount of the liquid phase of the injection solution to the ambient, the flow cross-section, i.e. the diameter of the radial bores 66 is be selected in dependence on the physical properties, in particular the specific density, the viscosity and the surface tension of the injection solution to be transferred from the syringe 14 to the injection device 10.

In order to ensure proper functioning of the venting device 64, the retention shoulders 23 protrude from the outer circumferential surface of the adapter element 18 in the region of the inlet section 26a and the intermediate section 26b of the through-opening 26 extending through the adapter element 18. Such a configuration ensures that, in the region of the receiving section 26c of the through-opening 26, an air gap 68 is present between the outer circumferential surface of the adapter element 18 and the inner circumferential surface of the hollow sleeve 16 which allows an unhindered exit of gas from receiving section 26c via the radial bores 66 of the venting device 64.

Figure 12:
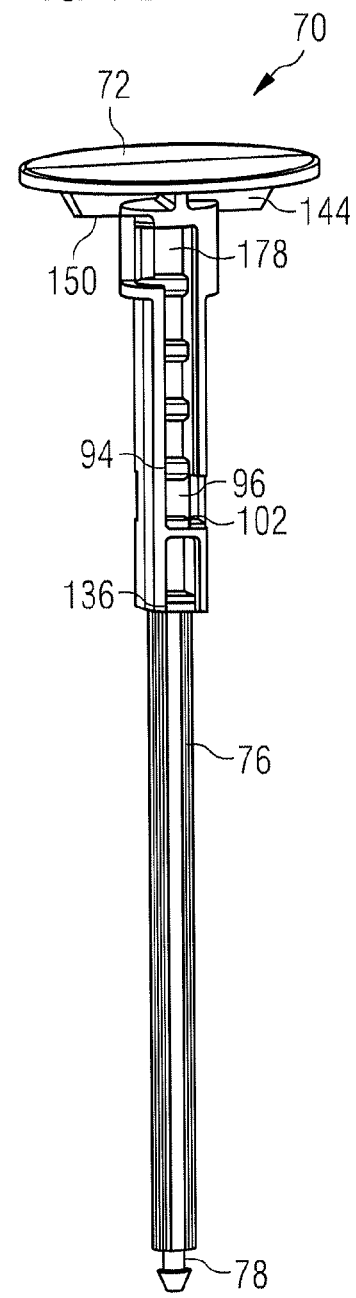
FIG. 12 shows a detailed view of the plunger of the injection device.

The injection device 10 of the injection solution transferring system 100 further comprises a plunger 70 which is depicted in greater detail in FIG. 12. In the embodiment of an injection device 10 shown in the drawings, the plunger 70 is made of polycarbonate. At least a portion of the plunger 70 is slidably received within the injection solution receptacle 30 of the injection device 10. The plunger 70 is displaceable relative to the injection solution receptacle 30 in a distal direction along a longitudinal axis of the plunger 70 in order to expel injection solution contained in the injection solution receptacle 30 of the injection device 10 from the injection solution receptacle 30. At its proximal end which protrudes from the injection solution receptacle 30 in a proximal direction, the plunger 70 carries an actuation button 72 which may be depressed by a user in order to displace the plunger 70 relative to the injection solution receptacle 30 in the distal direction along the longitudinal axis of the plunger 70.

Figure 13:
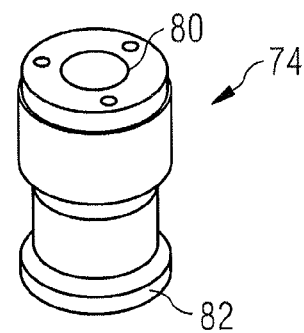
FIG. 13 shows a detailed view of a tip element of the plunger.

At its distal end, the plunger 70 is provided with a tip element 74 which is attached to a plunger rod 76, see FIG. 13. A coupling between the plunger rod 76 and the tip element 74 is effected by the interaction of a tip barb 78 provided at a distal end of the plunger rod 76 with a barb receptacle 80 of the tip element 74. Further, the tip element 74 is provided with a sealing element 82 which is provided in the region of an outer circumferential surface of the tip element 74 and which sealingly interacts with an inner circumferential surface of the injection solution receptacle 30.

Figure 14:
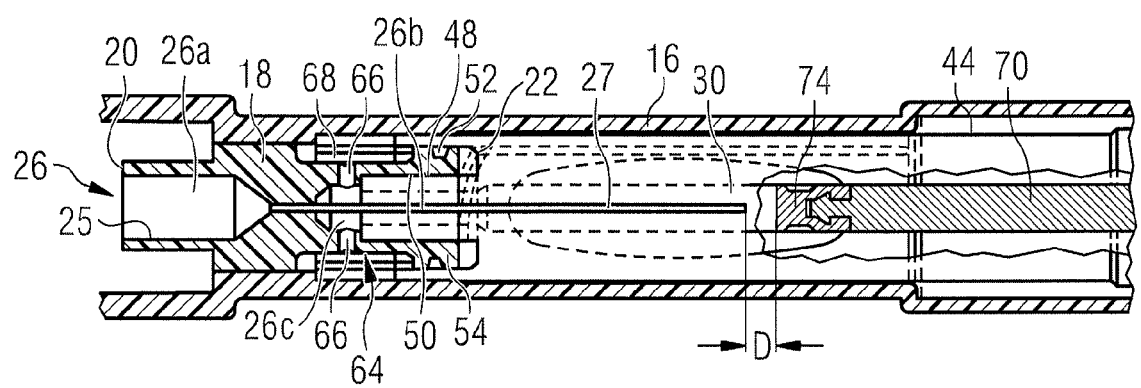
FIG. 14 shows the arrangement of the cannula of the filling adapter relative to the plunger of the injection device when the filling adapter is connected to the injection device.

The plunger 70 of the injection device 10 can be arranged in a filling position as shown in FIGS. 33a to 33d. When the plunger 70 is arranged in its filling position and the injection device 10 is engaged with the second connecting port 22 of the adapter element 18 of the filling adapter 12, a distal tip of the plunger 70, i.e. a distal end face of the tip element 74 provided at the distal tip of the plunger 70, is disposed at a desired close distance D from the distal tip of the cannula 27 of the filling adapter 12, see FIG. 14. For example, the injection device 10 and the filling adapter 12 may be designed so as to set the distance D between the distal tip of the plunger 70 and the distal tip of the cannula 27 to approximately 1.5 mm+/−0.5 mm. By arranging the distal tip of the plunger 70 and the distal tip of the cannula 27 at a close distance, the injection solution supplied to the injection solution receptacle 30 via the cannula 27 is reliably forced to flow in the direction of the venting device 64. As a result, air-free filling of the injection solution receptacle 30 with the injection solution can be ensured.

Finally, the hollow sleeve 16 is provided with two observing windows 83 for observing the filling of the injection device 10 with the injection solution from the syringe 14. The observing windows 83 allow an unhindered view of interior of the injection device 10 and the distal tip of the cannula 27.

The plunger 70 is displaceably received in a housing 84 of the injection device 10 which comprises a first housing element 86 depicted in greater detail in FIGS. 16 to 19 and a second housing element 88 depicted in greater detail in FIGS. 20 to 23. Both the first and the second housing element 86, 88 are made of polycarbonate/acrylnitril butadien styrol, but have a different colour. The first housing element 86 is provided with a plunger through-hole 90 which receives the plunger rod 76 so that the plunger 70 is displaceable in a direction along its longitudinal axis relative to the first housing element 86. Guiding elements 92 are provided on the first housing element 86 so as to protrude into the plunger through-hole 90. When the plunger 70, i.e. the plunger rod 76, is received in the plunger through-hole 90 of the first housing element 86, each guiding element 92 engages with a guiding channel 94 which provided in a circumferential surface of the plunger 70, i.e. the plunger rod 76, and which extends along the longitudinal axis of the plunger 70, see in particular FIGS. 19a and 19b.

For assembling the plunger 70 to the first housing element 86, assembly channels 96 are provided in the outer circumferential surface of the plunger rod 76 which branch of from the guiding channels 94 in a distal region thereof and extend substantially perpendicular to the guiding channels 94 in a circumferential direction of the plunger rod 76. Upon assembling the plunger 70 to the first housing element 86, the guiding elements 92 are brought into engagement with the assembly channels 96. Thereafter, the plunger 70 is rotated until the guiding elements 92 are received in the guiding channels 94 in a guiding manner, see FIGS. 19a and 19b.

In order to simplify the handling of the injection solution transferring system 100, the injection device 10 is delivered with the plunger 70 being arranged in its filling position which corresponds to a proximal end position of the plunger 70. A plunger positioning mechanism 98 prevents that the plunger 70 can be moved further in a proximal direction relative to the injection solution receptacle 30 than into its proximal end position, i.e. its filling position. The plunger positioning mechanism 98, however, allows a movement of the plunger 70 relative to the injection solution receptacle 30 from its filling position in a distal direction. Specifically, the plunger positioning mechanism 98 is defined by a distal end face 102 of the guiding channels 94 which are provided in the circumferential surface of the plunger rod 78 and the guiding elements 92 provided on the first housing element 86. When the plunger 70 is arranged in its proximal end position which corresponds to its filling position, the guiding elements 90 abut against the distal end faces 102 of the guiding channels 94. The interaction between the distal end faces 102 of the guiding channels 94 and the guiding elements 92 then prevents a further movement of the plunger 70 in the proximal direction and hence define the proximal end position, i.e. the filling position of the plunger 70.

Figure 20:
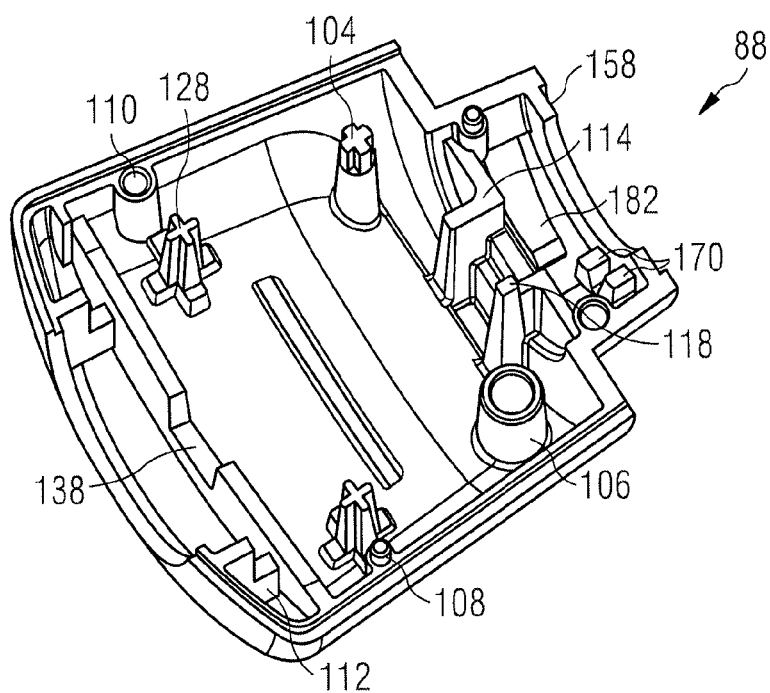
FIGS. 20 and 21 show detailed three-dimensional views of the second housing element of the injection device.
Figure 21:
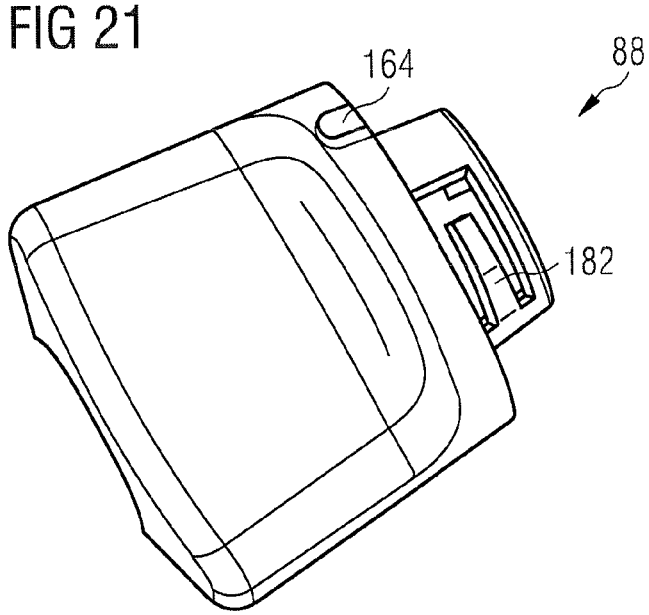
Figure 22:
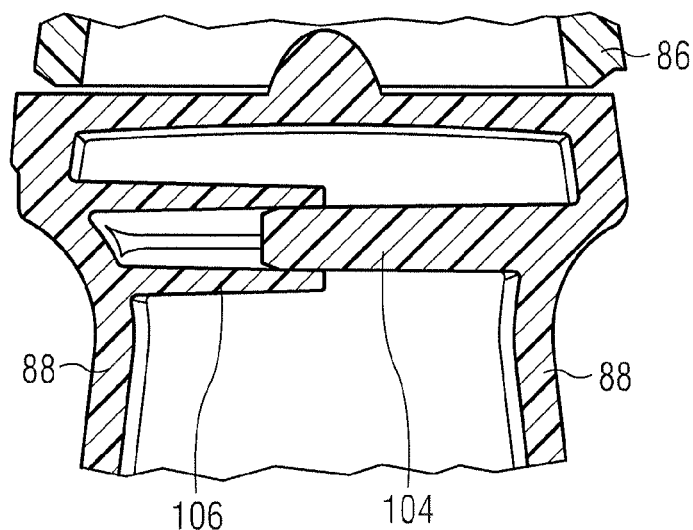
FIG. 22 shows the assembly of the second housing element.
Figure 23:
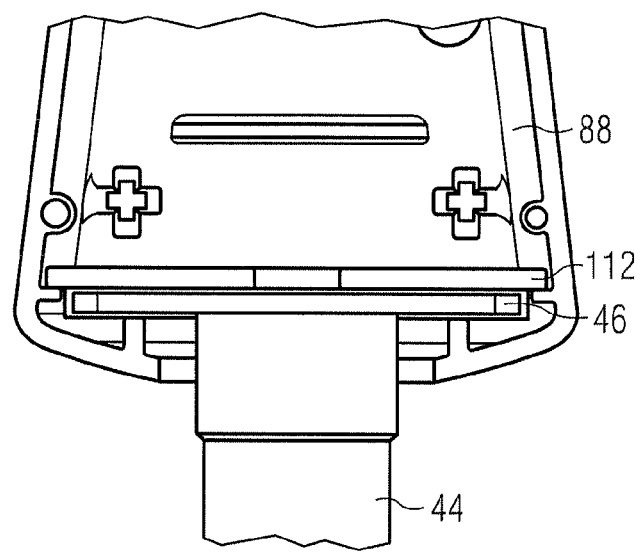
FIG. 23 shows the attachment of the injection solution receptacle to the second housing element.

The second housing element 88 comprises two identical parts, see FIGS. 20 and 21, each of which comprises an interference pin 104 and an interference receptacle 106. The two housing parts of the second housing element 88 are assembled by bringing the interference pins 104 into engagement with the respective interference receptacles 106 as shown in FIG. 22. For aligning the parts of the second housing element 88 relative to each other upon assembly, alignment pins 108 are provided which, upon connecting the parts of the second housing element 88, are received in respective alignment receptacles 110. The injection solution receptacle 30 and the protective outer barrel 44 are connected to the second housing element 88 via the flange element 46 which extends from the outer barrel 44 at a proximal end thereof. Specifically, the flange elements 46 is received in a suitably shaped and dimensioned receptacle 112 of the second housing element 88, see FIG. 23.

Figure 26:
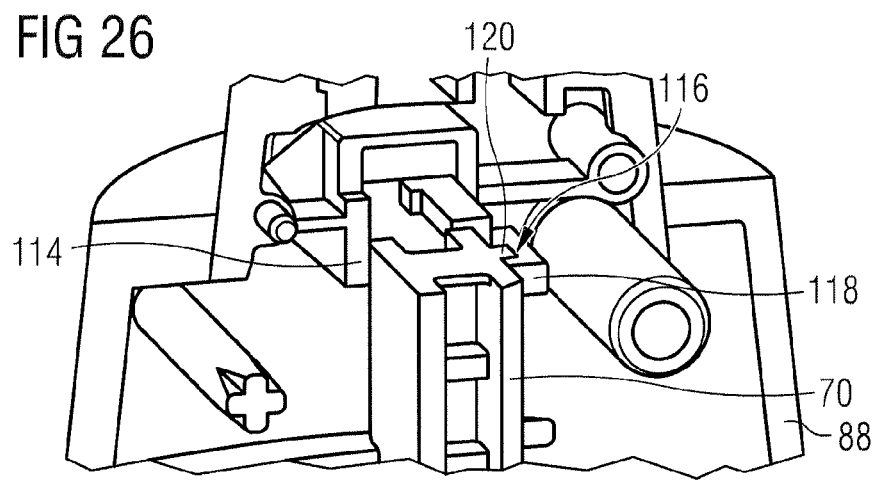
FIG. 26 shows the interaction between the plunger and the second housing element.

As shown in particular in FIG. 26, the second housing element 88 is provided with a plunger guide 114 which constrains the plunger rod 76 so that the plunger 70 is prevented from rotating relative to the second housing element 88. A first drag mechanism 116 is adapted to exert a retaining force which retains the plunger 70 in its current position relative to second housing element 88. The first drag mechanism 116 thus prevents an unintentional displacement of the plunger 70 relative to the injection solution receptacle 30 so that active manual actuation of the plunger 70, for example by the application of a pressing force to the actuation button 72, is necessary for displacing the plunger 70 relative to the injection solution receptacle 30. The first drag mechanism 116 comprises a resilient drag element 118 which is provided on the second housing element 88. The resilient drag element 118 exerts a resilient retaining force on the plunger 70, i.e. the resilient drag element 118 is resiliently urged out of a rest position into a biasing position by an interaction with the plunger 70 and, due to its resiliency, applies a resilient reaction force on the plunger 70 which retains the plunger 70 in its current position. Specifically, the resilient drag element 118 interacts with a drag rib 120 which is provided on the outer circumferential surface of the plunger rod 76 and which extends substantially parallel to the longitudinal axis of the plunger 70.

The injection device 10 further comprises a plunger locking mechanism 122 which interacts with the filling adapter 12, i.e. the hollow sleeve 16 of the filling adapter 12, so as to prevent the plunger 70 of the injection device 10 from being moved from its filling position relative to the injection solution receptacle 30 in a distal direction, i.e. in the direction of the distal tip of the cannula 27, when the injection device 10 is connected to the filling adapter 12. The plunger locking mechanism 122 serves to prevent an inadvertent contact between the plunger 70, i.e. the distal tip of the plunger 70, and the distal tip of the cannula 27. The functioning of the plunger locking mechanism 122 now will be described in greater detail with reference to FIGS. 27 to 32.

Figure 27:
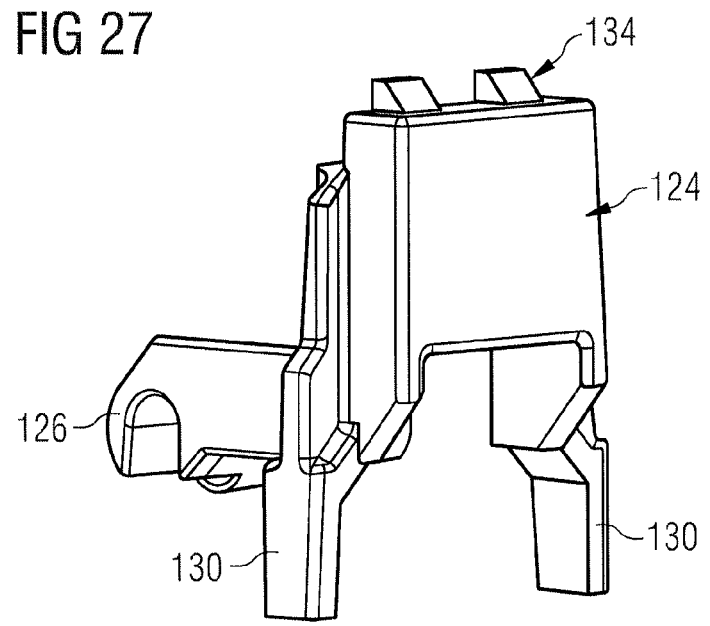
FIGS. 27 and 28 show detailed three-dimensional views of a lever element of a plunger locking mechanism which prevents the plunger of the injection device from being moved from a filling position in a distal direction when the injection device is connected to the filling adapter.
Figure 28:
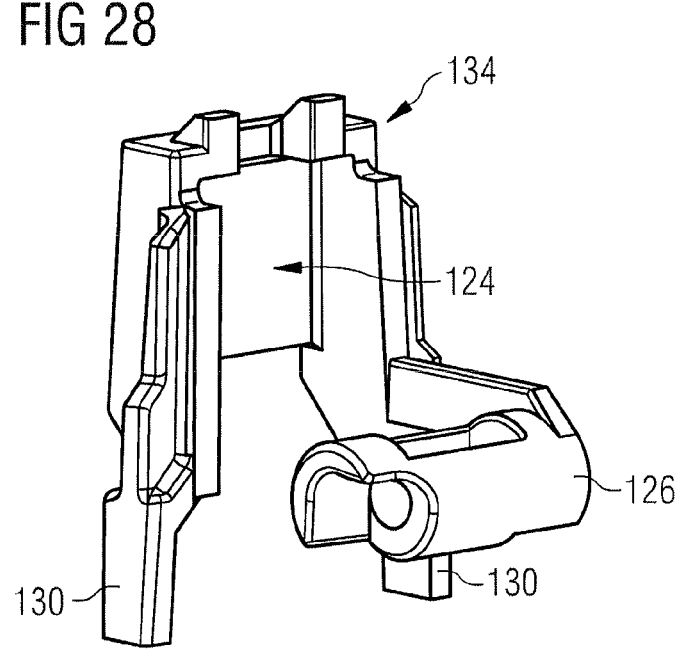
Figure 29:
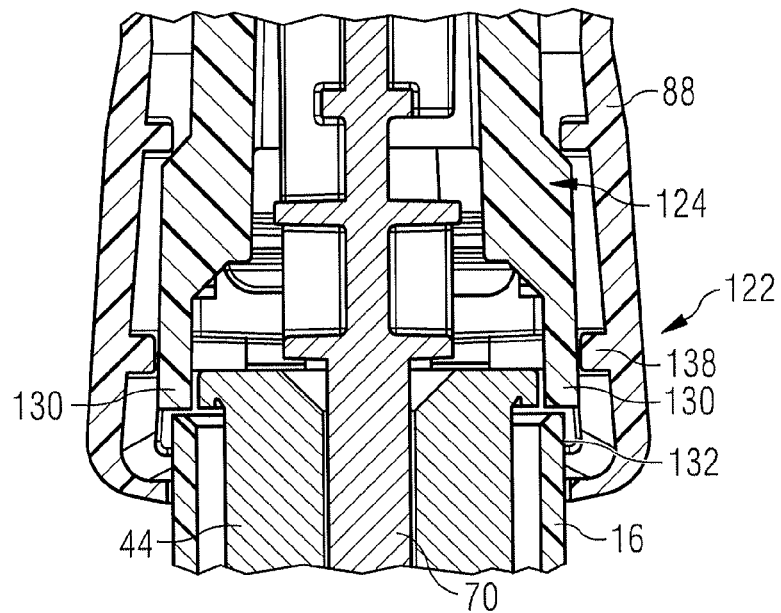
FIG. 29 shows the lever element of the plunger locking mechanism in an active position.
Figure 30:
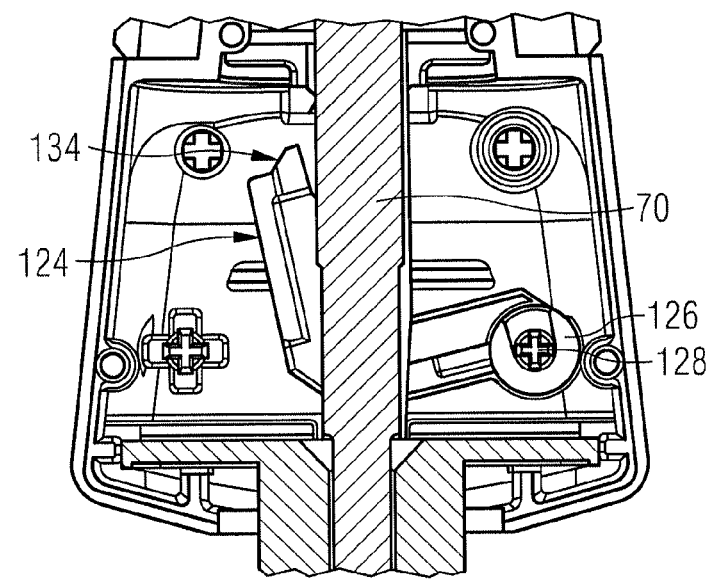
FIG. 30 shows the lever element of the plunger locking mechanism in an inactive position.
Figure 31:
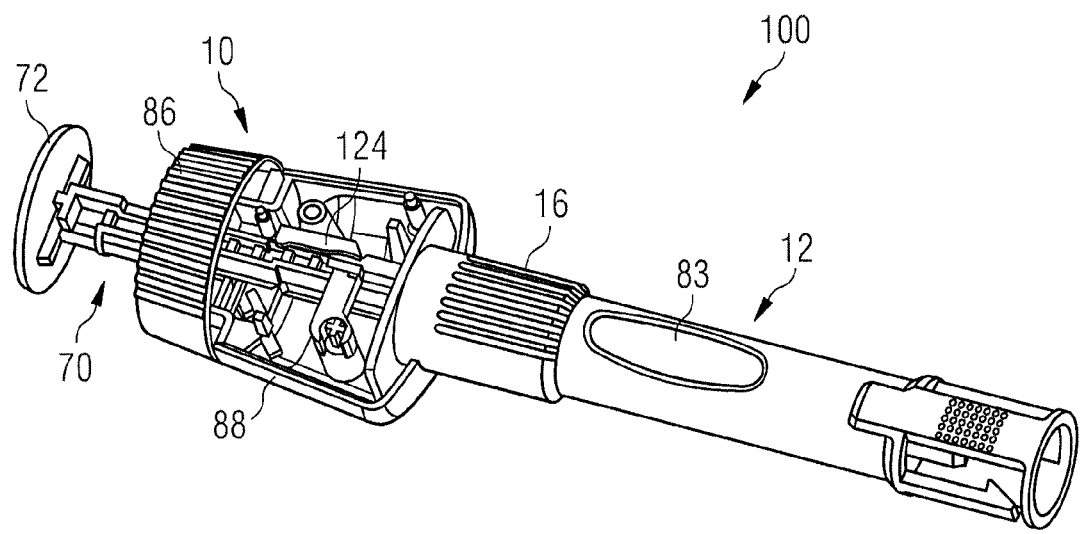
FIG. 31 shows the injection solution transferring system with the filling adapter being connected to the injection device, with one part of the second housing element removed and with the lever element of the plunger locking mechanism in its active position.

Specifically, the plunger locking mechanism 122 comprises a lever element 124, see FIGS. 27 and 28, which is displaceable within the second housing element 88 between an active position which is depicted in FIGS. 29 and 31 and an inactive position depicted in FIG. 30. When being arranged in its active position, the lever element 124 interacts with the plunger 70 and the hollow sleeve 16 of the filling adapter 12 so as to prevent the plunger 70 from being moved from its filling position in a distal direction when the injection device 10 is connected to the filling adapter 12. To the contrary, when being arranged in its inactive position, the lever element 124 allows a movement of the plunger 70 from its filling position in a distal direction when the injection device 10 is not connected to the filling adapter 12. The lever element 124 is mounted within the second housing element 88 so as to be rotatable between its active position and its inactive position. Specifically, the lever element 124 is provided with a hinge 126 which rotatably attaches the lever element 124 to a rotational axis 128 provided on the second housing element 88.

The lever element 124 further comprises a pair of foot elements 130 which extend substantially parallel to each other and which are contacted by the filling adapter 12 when the injection device 10 is connected to the filling adapter 12, in order to maintain the lever element 124 in its active position. In particular, as shown in FIG. 29, the foot elements 130 face the filling adapter 12 and are contacted by a locking rim 132 of the hollow sleeve 16 which faces the injection device 10 when the injection device 10 is connected to the filling adapter 12. Due to the interaction between the locking rim 132 of the hollow sleeve 16 and the foot elements 130, the lever element 124 is pushed in a proximal direction substantially parallel to the longitudinal axis of the plunger 70 into contact with the plunger 70 and thus held in its active position shown in FIGS. 29 and 31.

The lever element 124 comprises a stop device 134 which comprises two tabs extending from a proximal end face of the lever element 124. Further, a proximal portion of the plunger 70 extends further in a direction substantially perpendicular to the longitudinal axis of the plunger 70 than a distal portion of the plunger 70. As a result, a shoulder which defines an abutment surface 136 is formed in a transition region between the distal portion and the proximal portion of the plunger 70. Specifically, the abutment surface 136 is defined by an outer portion of a distal end face of the proximal plunger portion which protrudes from an outer circumferential surface of the distal plunger portion. When the lever element 124 is arranged in its active position as shown in FIG. 29, the two tabs of the stop device 134 abut against the abutment surface 136 of the plunger 70. As a result, the lever element 124 is held in its active position and, simultaneously, movement of the plunger 70 from its filling position in a distal direction is prevented.

Figure 32:
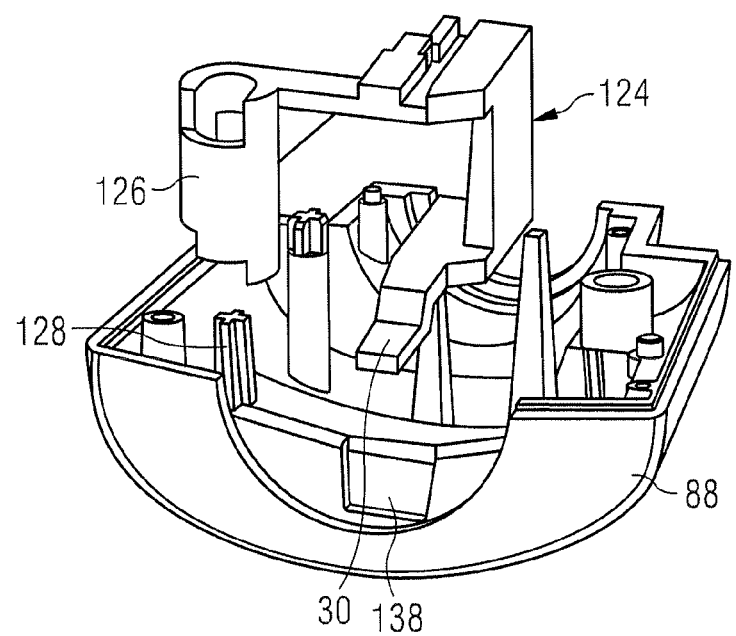
FIG. 32 shows the assembly of the lever element of the plunger locking mechanism in the second housing element.

The plunger locking mechanism 122 also comprises a retention device 138 which interacts with the foot elements 130 of the lever element 124, in order to prevent that the foot elements 130 disengage from locking rim 132 of the filling adapter 12 when the lever element 124, by the interaction between the locking rim 132 and the foot elements 130, is maintained in its active position, see FIGS. 20 and 32. In particular, the retention device 138 prevents that the foot elements 130 slip around the locking rim 132 of the hollow sleeve 16 and hence disengages from the filling adapter 12 when the lever element 124 is pushed into engagement with the plunger 70. The retention device is provided in the second housing element 88 and is designed in the form of a retention rib which prevents that the foot elements 130 of the lever element 124 deform away from the plunger 70 in a direction substantially perpendicular to the longitudinal axis of the plunger 70.

After completion of the transfer of the injection solution from the syringe 14 to the injection solution receptacle 30 of the injection device 10 with the plunger 70 being arranged in its filling position as described above and as shown in FIGS. 33a to 33c, the filling adapter 12 and the syringe 14 are detached from the injection device 10 by disengaging the male Luer taper 48 provided at the distal end of the injection solution receptacle 30 from the female Luer taper 50 provided on the second connecting port 22 of the adapter element 18 and by disengaging the Luer thread 52 provided at the distal end of the outer barrel 44 from the complementary Luer thread 54 provided at the second connecting port 22, see FIG. 33d.

As soon as the filling adapter 12 is detached from the injection device 10, the filling adapter 12, i.e. the locking rim 132 of the hollow sleeve 16, no longer contacts the foot elements 130 of the lever element 124. Hence, when a pressing force is applied to the plunger 70 so as to displace the plunger 70 in a distal direction within the injection solution receptacle 30 of the injection device 10, the lever element 124 is displaced into its inactive position shown in FIG. 30. In particular, the lever element 124 is rotated around its rotational axis 128 from its active position into its inactive position and hence out of the way of the plunger 70. As a result, the displacement of the plunger 70 is no longer hindered. Consequently, a needle (not shown in the drawings) can be attached to the injection device 10, for example with the aid of the Luer thread 52 provided at the distal end of the outer barrel 44 and injection device 10 can be operated as will be described further below.

For administering an accurate dose, in particular an accurate micro dose of, for example, 10 μl of the injection solution received within the injection solution receptacle 30 to a patient, in a first step, excess injection solution has to be expelled from the injection solution receptacle 30 by displacing the plunger 70 relative to the injection solution receptacle 30 in the distal direction as shown in FIG. 34a. Thereafter, the desired to dose of the injection solution has to be injected into the patient.

The injection device 10 therefore comprises a first plunger stop mechanism 140 which is adapted to stop a displacement of the plunger 70 relative to the injection solution receptacle 30 in the distal direction at a first dosing position P1, see FIG. 34. Further, the injection device 10 comprises a second plunger stop mechanism 142 which is adapted to stop a displacement of the plunger 70 relative to the injection solution receptacle 30 from the first dosing position P1 in the distal direction at a second dosing position P2, see FIG. 34d. The first and the second dosing position P1, P2 of the plunger 70 are selected in such a manner that the plunger 70, upon being displaced relative to the injection solution receptacle 30 between the first and the second dosing position P1, P2 is adapted to expel a desired dose of the injection solution contained in the injection solution receptacle 30 from the injection solution receptacle 30.

Thus, during use of the injection device 10, a user can expel excess injection solution from the injection solution receptacle 30 by displacing the plunger 70 relative to the injection solution receptacle 30 in the distal direction until the plunger 70 reaches the first dosing position P1. Upon reaching the first dosing position P1, the first plunger stop mechanism stops 140 further displacement of the plunger 70 in the distal direction. Consequently, the user is prevented from expelling too much injection solution from the injection solution receptacle. The residual injection solution contained in the injection solution receptacle can then be administered to a patient by further displacing the plunger 70 in the distal direction until the plunger 70 reaches the second dosing position P2. Upon reaching the second dosing position P2, the second plunger stop mechanism 142 stops further displacement of the plunger 70 in the distal direction and hence prevents that too much injection solution is administered to the patient.

Figure 16:
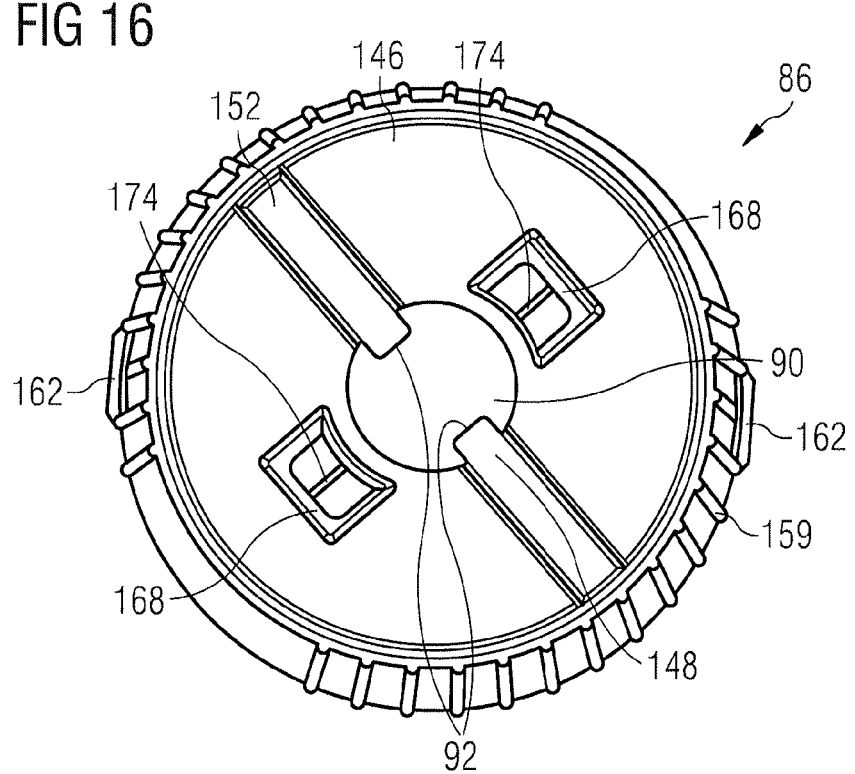
FIGS. 16 to 18 show detailed three-dimensional views of a first housing element of the injection device.
Figure 18:
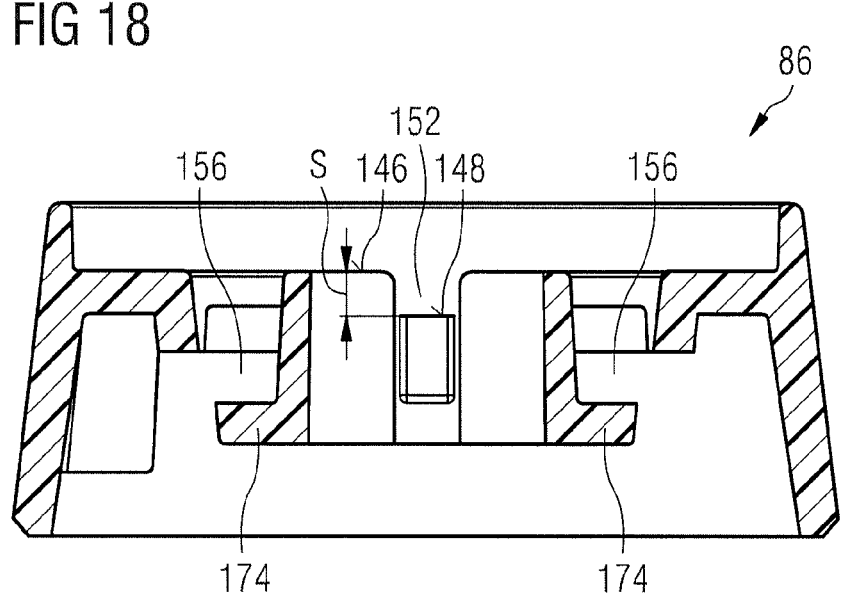

As shown in particular in FIGS. 12, 16 and 18, the first plunger stop mechanism 140 comprises a dosing element 144 which is attached to the plunger 70 and which is adapted to abut against a first dosing surface 146 provided on the first housing element 86. The dosing element 144 also forms a part of the second plunger stop mechanism 142 and, as a part of the second plunger stop mechanism 142, is adapted to abut against a second dosing surface 148 which is also provided on the first housing element 86. The dosing element 144 is formed integral with the plunger 70 and is designed in the form of a rib protrudes from a lower surface of the activation button 72 in the direction of the inner solution receptacle 30.

The first and the second dosing surface 146, 148 extend substantially parallel to each other and parallel to an abutting surface 150 of the dosing element 144 substantially perpendicular to the longitudinal axis of the plunger 70, wherein the second dosing surface 148 is arranged parallel offset relative to the first dosing surface 146 in the distal direction. A distance S between the first and the second dosing surface 146, 148 in the distal direction corresponds to a desired travel distance of the plunger 70 in the distal direction between the first and the second dosing position P1, P2, see in particular FIG. 18. Hence, the distance S between the first and the second dosing surface 146, 148 in the distal direction sets the desired injection solution dose to be expelled from the injection solution receptacle 30 upon displacing the plunger 70 from the first to the second dosing position P1, P2.

Further, the first and the second dosing surface 146, 148 are arranged offset relative to each other in a circumferential direction of the plunger 70. Specifically, the second dosing surface 148 is defined by a bottom surface of a recess 152 formed in the first dosing surface 146 provided on the first housing element 86.

When the plunger 70, during use of the injection device 10, is moved from its filling position shown in FIG. 34*a* in the distal direction, the abutting surface 150 of the dosing element 144 abuts against the first dosing surface 146 when the plunger 70 reaches the first dosing position P1 as depicted in FIG. 34*b*. The interaction of the dosing element 144 with the first dosing surface 146 prevents the plunger from being displaced further in the distal direction. Hence, the first plunger stop mechanism 140 provides a hard stop for the plunger 70 at the first dosing position P1. The injection device 10 therefore further comprises a plunger releasing mechanism 154 which is adapted to deactivate the first plunger stop mechanism 140 in order to release the plunger 70 and to thus allow a displacement of the plunger 70 relative to the injection solution receptacle 30 from the first dosing position P1 in the distal direction, i.e. in the direction of the second dosing position P2.

The plunger releasing mechanism 154 is adapted to allow a movement of the first dosing surface 146 relative to the dosing element 144, i.e. relative to the plunger 70, in order to disengage the dosing element 144 from the first dosing surface 146. Specifically, the plunger releasing mechanism 154 is adapted to allow a rotational movement of the first dosing surface 146 relative to the dosing element 144, i.e. relative to the plunger 70, in order to disengage the dosing element 144 from the first dosing surface 146. In order to effect the rotational movement of the first dosing surface 146 relative to the dosing element 144, the first housing element 86 which carries the first and the second dosing surface 146, 148 is designed so as to be manually rotatable relative to the second housing element 88, see FIG. 34*c*. Since the plunger 70 is prevented from rotating relative to the second housing element 88 by means of the plunger guide 114, a rotation of the first housing element 86 relative to the second housing element 88 inevitably results in a rotation of the first housing element 86 relative to the plunger 70.

Figure 17:
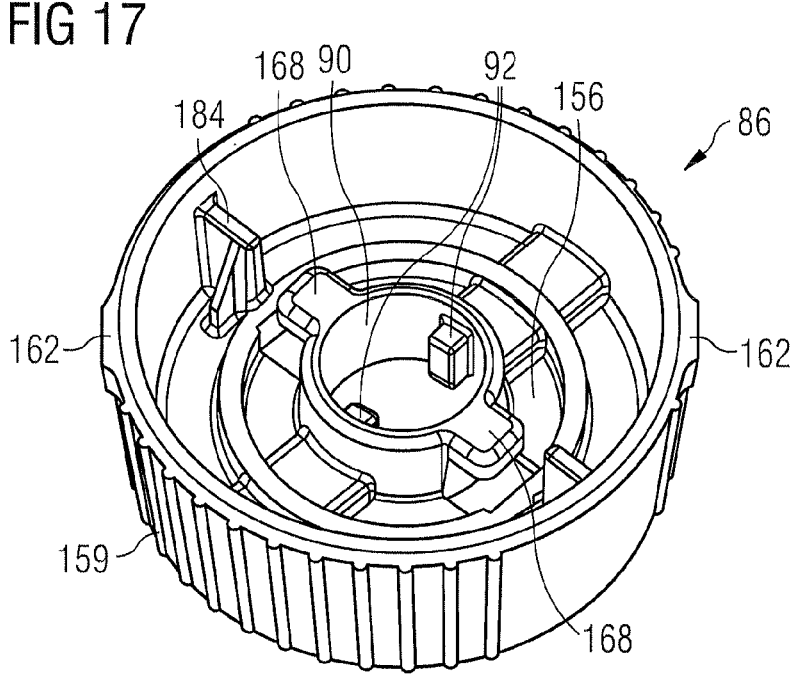
Figure 24:
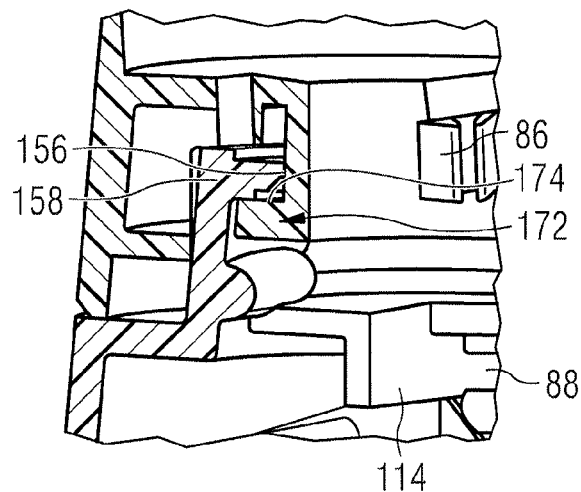
FIGS. 24 and 25 show the interaction between the first and the second housing element.

In order to be rotatable relative to the second housing element 88 in a guided manner, the first housing element 86 is provided with a retaining recess 156, see FIGS. 17, 18 and 24, which receives a retaining element 158 formed on the second housing element 88, see FIG. 20. Further, in order to simplify the handling of the plunger releasing mechanism 154, the first housing element 86, in the region of its outer surface, is provided with a gripping structure 159. The gripping structure 159 is designed in the form of a gripping rib array with individual gripping ribs extending substantially in a direction along the longitudinal axis of the plunger 70.

The rotation amount of the first housing element 86 relative to the second housing element 88 and hence relative to the plunger 70 is set such that the recess 152 formed in the first dosing surface 146 is brought into alignment with the dosing element 144 protruding from the activation button 72 of the plunger 70. The plunger releasing mechanism 154 thus is adapted to displace the first and the second dosing surface 146, 148 in the circumferential direction of the plunger 70, in order to disengage the dosing element 144 from the first dosing surface 146 and to simultaneously align the second dosing surface 148 with the dosing element 144.

In order to ensure that a user, upon activating the plunger releasing mechanism 154, rotates the first housing element 86 relative to the second housing element 88 and the correct direction and by the correct rotation amount that is necessary to disengage the dosing element 144 from the first dosing surface 146 and to simultaneously align the second dosing surface 148 with the dosing element 144, the plunger releasing mechanism 154 comprises a marker system 160 which is adapted to indicate an activation of the plunger releasing mechanism 154. The marker system 160 comprises a first marker element 162 which is provided on an outer surface of the first housing element 86. The marker system 160 further comprises a second marker element 164 which is provided on an outer surface of the second housing element 88. The first and the second marker element 162, 164 are arranged on the first and the second housing element 86, 88 in such a position that they are positioned offset relative to each other a circumferential direction of the plunger 70, when the plunger release mechanism 154 is not activated, but positioned in alignment with each other, when the plunger release mechanism 154 is activated, compare FIGS. 34*b* and 34*c*.

The injection device 10 further comprises a limiting mechanism 166 which is adapted to limit the movement of the first and the second dosing surface 146, 148 for disengaging the dosing element 144 from the first dosing surface 146 and for aligning the dosing element 144 with the second dosing surface 146, see FIGS. 16 and 20. The limiting mechanism 166 comprises a first limiting element 168 which is provided on the first housing element 86 carrying the first and the second dosing surface 146, 148. Further, the limiting mechanism 166 comprises a second limiting element 170 which is provided on the second housing element 88 which remains stationary when the first housing element 86 is rotated in order to deactivate the first plunger stop mechanism 140. The first limiting element 168 abuts against the second limiting element 170 when the dosing element 144, due to the rotation of the first housing element 86 relative to plunger 70, is disengaged from the first dosing surface 146 and aligned with the second dosing surface 148. The limiting mechanism 166 prevents a user of the injection device 10 from excessively rotating the first housing element 86 relative to the second housing element 88. Further, the limiting mechanism 166 provides an haptic feedback to the user that the first plunger stop mechanism 140 has been deactivated.

A second drag mechanism 172 serves to exert a retaining force which retains the first housing element 86 in its current position relative to the second housing element 88. Due to the presence of the second drag mechanism 172, active manual actuation is necessary for rotating the first housing element 86 relative to the second housing element 88. The second drag mechanism 172 thus prevents an unintentional displacement of the first housing element 86 relative to the second housing element 88 and hence an unintentional activation of the plunger releasing mechanism 154. The second drag mechanism 172 comprises a friction element 174 which is provided on the first limiting element 168 of the limiting mechanism 166 and which is adapted to frictionally interact with the retaining element 158 of the second housing element 88.

Figure 19A:
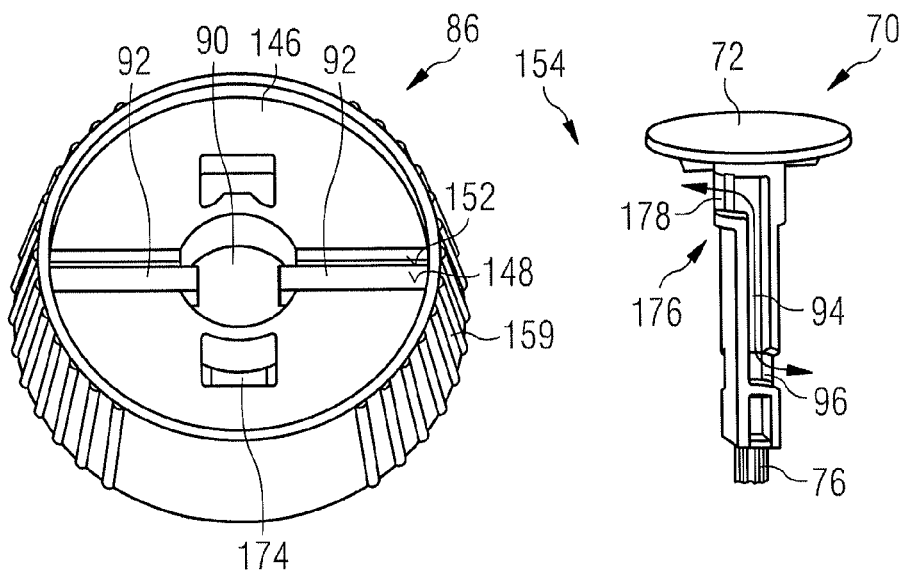
FIGS. 19a and 19b show the interaction between the plunger and the first housing element.
Figure 19B:
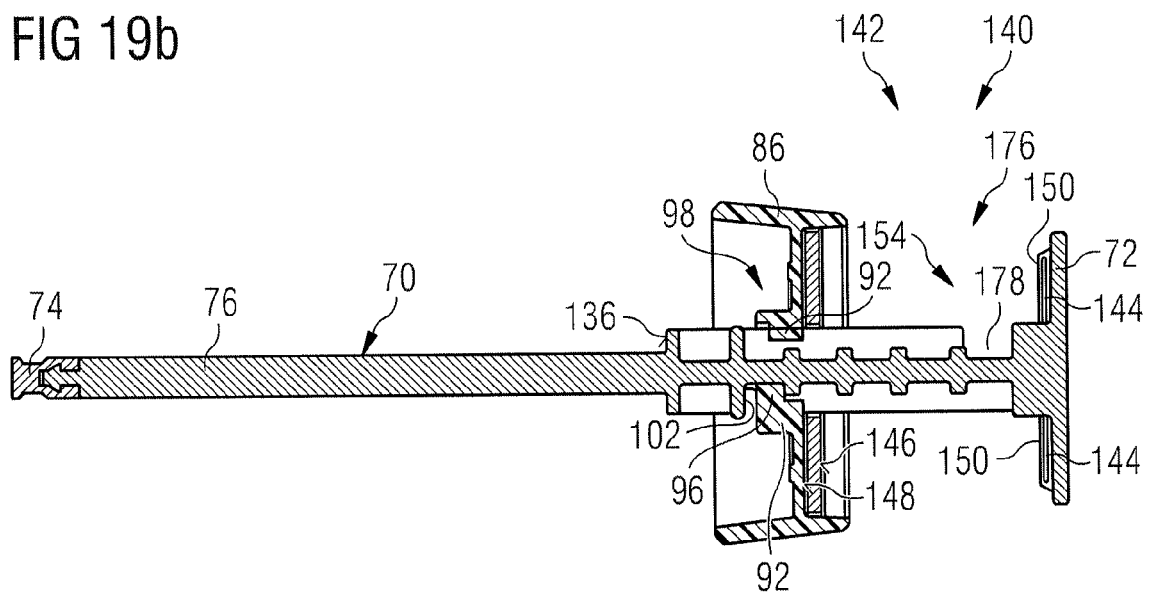

The injection device 10 further comprises an activation mechanism 176 which is adapted to prevent an activation of the plunger releasing mechanism 154 unless the plunger 70 is arranged at the first dosing position P1 and which is adapted to allow an activation of the plunger releasing mechanism 154 when the plunger 70 is arranged at the first dosing position P1 see FIGS. 12, 16 and 19*a*. Specifically, the activation mechanism 176 prevents a rotation of the first housing element 86 relative to the plunger 70 and hence prevents a movement of the dosing element 144 and the first dosing surface 144 relative to each other unless the plunger 70 is arranged at the first dosing position P1.

The activation mechanism 176 comprises the guiding channel 94 which is provided on the circumferential surface of the plunger 70, which extends along the longitudinal axis of the plunger 70 and which receives the guiding element 92 provided on the first housing element 86 in such a manner that the guiding channel 94, upon displacement of the plunger 70 relative to the injection solution receptacle 30, is displaced relative to the guiding element 92. An interaction between the guiding element 92 and opposing side surfaces of the guiding channel 94 prevents a rotation of the plunger 70 and the first housing element 86 relative to each other. The activation mechanism 176 thus fulfills the double function to provide for a guided displacement of the plunger 70 in the direction of its longitudinal axis on the one hand and to simultaneously prevent an unintentional deactivation of the first plunger stop mechanism 154 when the plunger 70 is not arranged at the first dosing position.

The activation mechanism 176 further comprises an activation channel 178 which branches off from the guiding channel 94 and extends in a circumferential direction of the plunger 70 substantially perpendicular to the guiding channel 94. The activation channel 178 receives the guiding element 92 when the plunger 70 is arranged at the first dosing position P1 and the first housing element 86 is rotated relative to the plunger 70. Hence, the first dosing position P1 of the plunger 70 is defined by the position of the activation channel 178 along the longitudinal axis of the plunger 70.

Figure 25:
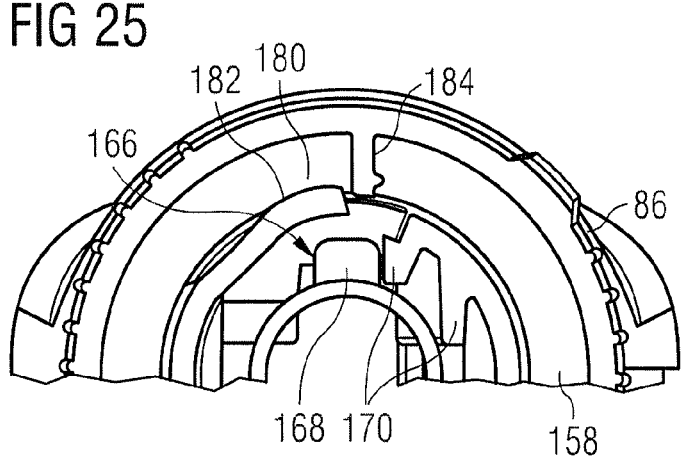

Finally, the plunger release mechanism 154 further comprises a locking arrangement 180 which locks the first dosing surface 146 in its position relative to the dosing element 144 after the first dosing surface 146 has been moved relative to the dosing element 144 in order to become disengaged from the dosing element 144, see FIGS. 17, 21 and 25. Specifically, the locking arrangement 180 comprises a resilient locking clip 182 which is provided on the second housing element 88 and which is resiliently urged out of a rest position by the interaction with a locking element 184 provided on the first housing element 86 when the first dosing surface 146 is moved relative to the dosing element 144 so as to become disengaged from the dosing element 144, i.e. when the first housing element 86 is rotated relative to the second housing element 88.

The locking clip 182 deforms back into its rest position after completion of the movement of the first dosing surface 146, i.e. after completion of the rotation of the first housing element 86, and interacts with the locking element 184 so as to lock the first housing element 86 relative to the second housing element 88 and the plunger 70. In particular, the locking clip 182 interacts with the locking element 184 so as to prevent a counter rotation of the first housing element 86 relative to the second housing element 88 and the plunger 70, after the first housing element 86 has been rotated once in order to disengage the first dosing surface 146 from the dosing element 144 and to align the second dosing surface 148 with the dosing element 144. Consequently, the first dosing surface 146 is locked in its position relative to the dosing element 144. The locking arrangement 180 allows the plunger release mechanism 154 to be used only once for deactivating the first plunger stop mechanism 140. As a result, reuse of the injection device 10 is prevented.

After completion of the rotational movement of the first housing element 86 relative to the second housing element 88 with the plunger 70 being arranged in its first dosing position P1, the dosing element 144 is aligned with the recess 152 formed in the first dosing surface 146. Consequently, the abutting surface 150 of the dosing element 144 is arranged parallel to the second dosing surface 148 at the distance S. As a result, the plunger 70 can further be displaced from the first dosing position P1 in the distal direction by the distance S into the second dosing position P2, until the dosing element 144, i.e. its abutting surface 150 abuts against the second dosing surface 148, compare FIGS. 34c and 34d. Like the first plunger stop mechanism 140, also the second plunger stop mechanism 142 provides a hard stop for the plunger 70, i.e. prevents the plunger 70 from being displaced relative to the injection solution receptacle 30 from the second dosing position P2 in the distal direction. The dose of the injection solution to be administered to a patient can thus be set in a particularly accurate manner.

LIST OF REFERENCE NUMERALS injection solution transferring system 100
injection device 10
filling adapter 12
syringe 14
hollow sleeve 16
adapter element 18
first connecting port 20
second connecting port 22
retention shoulders 23
crush ribs 24
female Luer taper (of the first connecting port) 25
through-opening 26
inlet section (of the through-opening) 26a
intermediate section (of the through-opening) 26b
receiving section (of the through-opening) 26c
longitudinal axis (of the filling adapter) L1
longitudinal axis (of the injection device) L2
cannula 27
plunger (of the syringe) 28
injection solution receptacle 30
resilient clip 32
collar (of the syringe) 34
arm (of the resilient clip) 36
recess 38
latching nose (of the resilient clip) 40
first gripping structure 42
outer barrel 44
flange element 46
male Luer taper (of the injection solution receptacle) 48
female Luer taper (of the second connecting port) 50
Luer thread (of the outer barrel) 52
Luer thread (of the second connecting port) 54
second gripping structure 56
guiding ribs 58
venting device 64
radial bore 66
air gap 68
plunger 70
actuation button 72
tip element 74
plunger rod 76
tip barb 78
barb receptacle 80
sealing element 82
distance distal tip plunger/distal tip cannula D
observing windows 83
housing 84
first housing element 86
second housing element 88
plunger through-hole 90
guiding element 92
guiding channel 94 assembly channel 96
plunger positioning mechanism 98
distal end face (of the guiding channel) 102
interference pin 104
interference receptacle 106
alignment pin 108
alignment receptacle 110
receptacle (for receiving flange element) 112
plunger guide 114
first drag mechanism 116
resilient drag element 118
drag rib 120
plunger locking mechanism 122
lever element 124
hinge 126
rotational axis 128
foot elements 130
locking rim 132
stop device 134
abutment surface (of the plunger) 136
retention device 138
first plunger stop mechanism 140
second plunger stop mechanism 142
first dosing position P1
second dosing position P2
dosing element 144
first dosing surface 146
second dosing surface 148
distance first dosing surface/second dosing surface S
abutting surface (of the dosing element) 150
recess 152
plunger releasing mechanism 154
retaining recess 156
retaining element 158
gripping structure 159
marker system 160
first marker element 162
second marker element 164
limiting mechanism 166
first limiting element 168
second limiting element 170
second drag mechanism 172
friction element 174
activation mechanism 176
activation channel 178
locking arrangement 180
resilient locking clip 182
locking element 184

The invention claimed is:

1. An injection device, comprising:
an injection solution receptacle;
a plunger at least a portion of which is slidably received in the injection solution receptacle, wherein the plunger is displaceable relative to the injection solution receptacle in a distal direction in order to expel an injection solution contained in the injection solution receptacle from the injection solution receptacle;
a first housing element, wherein:
a first dosing surface, a first limiting element and a second dosing surface are formed on the first housing element;
a first plunger stop mechanism which is adapted to stop a displacement of the plunger relative to the injection solution receptacle in the distal direction at a first dosing position, wherein the first plunger stop mechanism includes a dosing element which is attached to the plunger and which is adapted to abut against the first dosing surface; and
a second plunger stop mechanism which is adapted to stop a displacement of the plunger relative to the injection solution receptacle from the first dosing position in the distal direction at a second dosing position, wherein:
the second plunger stop mechanism includes the dosing element which is attached to the plunger and which is adapted to abut against the second dosing surface,
the first housing element is rotatable relative to the plunger to a position that disengages the dosing element of the first plunger stop mechanism from the first dosing surface and aligns the second dosing surface with the dosing element,
the first limiting element prevents rotation of the dosing element past the second dosing surface, and
the first and the second dosing position of the plunger are selected in such a manner that the plunger, upon being displaced relative to the injection solution receptacle between the first and the second dosing position is adapted to expel a desired dose of the injection solution contained in the injection solution receptacle from the injection solution receptacle.

2. The injection device of claim 1, wherein rotation of the first housing element relative to the plunger moves at least one of the dosing element and the first dosing surface in order to disengage the dosing element from the first dosing surface.

3. The injection device of claim 1, wherein the first and the second dosing surface are arranged offset relative to each other in a circumferential direction of the plunger, and wherein rotation of the first housing element displaces the first and the second dosing surface in the circumferential direction of the plunger, in order to disengage the dosing element from the first dosing surface and to simultaneously align the second dosing surface with the dosing element such that the dosing element abuts against the second dosing surface, when the plunger, upon being displaced relative to the injection solution receptacle from the first dosing position in the distal direction, reaches the second dosing position.

4. The injection device of claim 1, further comprising a marker system that is adapted to indicate an alignment of the dosing element with the second plunger stop mechanism, wherein a first marker element of the marker system is positioned on the first housing element.

5. The injection device of claim 1, further comprising:
an activation mechanism which is adapted to prevent rotation of the first housing element relative to the plunger unless the plunger is arranged at the first dosing position and which is adapted to allow rotation of the first housing element relative to the plunger when the plunger is arranged at the first dosing position.

6. The injection device of claim 5, wherein the activation mechanism comprises a guiding channel which is provided on a circumferential surface of the plunger, which extends along a longitudinal axis of the plunger and which receives a guiding element provided on the first housing element in such a manner that the guiding channel, upon displacement of the plunger relative to the injection solution receptacle, is displaced relative to the guiding element, and wherein an interaction between the guiding element and opposing side faces of the guiding channel prevents a rotation of the plunger and the first housing element relative to each other.

7. The injection device of claim 6, wherein the activation mechanism further comprises an activation channel which branches off from the guiding channel and which is adapted to receive the guiding element when the plunger is arranged at the first dosing position and the first housing element which carries the guiding element is rotated relative to the plunger.

8. The injection device of claim 1, further comprising a locking arrangement which is adapted to lock the first dosing surface in its position relative to the dosing element after the first dosing surface has been moved relative to the dosing element in order to become disengaged from the dosing element.

9. The injection device of claim 8, wherein the locking arrangement comprises a resilient locking clip which is adapted to be resiliently urged out of a rest position by the interaction with a locking element when the first dosing surface is moved relative to the dosing element so as to become disengaged from the dosing element, and which further is adapted to deform back into its rest position after completion of the movement of the first dosing surface and to interact with the locking element so as to lock the first dosing surface in its position relative to the dosing element.

10. The injection device of claim 1, wherein the first limiting element is adapted to abut against a second limiting element when the dosing element is disengaged from the first dosing surface and aligned with the second dosing surface and wherein the second limiting element is configured to remain stationary during rotation of the first housing element relative to the plunger.

11. The injection device of claim 1, further comprising at least one of:
a first drag mechanism adapted exert a retaining force which retains the plunger in its current position, the first drag mechanism in particular comprising a resilient drag element which is adapted to exert a resilient retaining force on the plunger; and
a second drag mechanism adapted to exert a retaining force which retains the first housing element in its current position, the second drag mechanism in particular comprising a friction element which is provided on the first limiting element of the limiting mechanism and which is adapted to interact with a retaining element of the second housing element.

12. The injection device of claim 1, further comprising:
a plunger positioning mechanism comprising a distal end of a guiding channel provided in a circumferential surface of the plunger, which is adapted to prevent a displacement of the plunger relative to the injection solution receptacle from a proximal end position in a proximal direction.

13. An injection solution transferring system, comprising:
an injection device according to claim 1; and
a filling adapter for connecting a syringe containing an injection solution to the injection device and for filling an injection solution receptacle of the injection device with the injection solution from the syringe.

* * * * *